United States Patent [19]
Hossack et al.

[11] Patent Number: 5,924,991
[45] Date of Patent: Jul. 20, 1999

[54] ULTRASONIC SYSTEM AND METHOD FOR HARMONIC IMAGING IN THREE DIMENSIONS

[75] Inventors: John A. Hossack, Palo Alto; Samuel H. Maslak, Woodside, both of Calif.

[73] Assignee: Acuson Corporation, Mountain View, Calif.

[21] Appl. No.: 09/137,070

[22] Filed: Aug. 20, 1998

Related U.S. Application Data

[62] Division of application No. 08/924,407, Aug. 22, 1997.

[51] Int. Cl.$^6$ ....................................................... A61B 8/00
[52] U.S. Cl. ........................................... 600/443; 128/916
[58] Field of Search ..................................... 600/437, 441, 600/443, 447, 458; 367/70, 126

[56] References Cited

U.S. PATENT DOCUMENTS

| | | |
|---|---|---|
| 3,640,271 | 2/1972 | Horton . |
| 4,100,916 | 7/1978 | King . |
| 4,702,258 | 10/1987 | Nicolas et al. .......................... 600/443 |
| 4,712,037 | 12/1987 | Verbeek et al. . |
| 4,714,846 | 12/1987 | Pesque et al. .......................... 310/317 |
| 4,849,692 | 7/1989 | Blood . |
| 4,945,305 | 7/1990 | Blood . |
| 5,034,931 | 7/1991 | Wells ..................................... 367/126 |
| 5,040,537 | 8/1991 | Katakura . |
| 5,111,823 | 5/1992 | Cohen . |
| 5,115,809 | 5/1992 | Saitoh et al. . |
| 5,127,409 | 7/1992 | Daigle . |
| 5,135,000 | 8/1992 | Akselrod et al. . |
| 5,159,931 | 11/1992 | Pini . |
| 5,190,766 | 3/1993 | Ishihara . |
| 5,195,520 | 3/1993 | Schlief et al. . |
| 5,195,521 | 3/1993 | Melton, Jr. et al. ..................... 600/438 |
| 5,197,477 | 3/1993 | Peterson et al. . |
| 5,215,680 | 6/1993 | D'Arrigo . |
| 5,219,401 | 6/1993 | Cathignol et al. . |

(List continued on next page.)

FOREIGN PATENT DOCUMENTS 357 164 of 0000 European Pat. Off. .
770 352 A1 5/1997 European Pat. Off. .
846 442 A2 6/1998 European Pat. Off. .

OTHER PUBLICATIONS

Schwartz, G.A. UTS Diagnostic Imaging System for LV Function Analysis EP0846442 Publ. Oct. 6, 1998 Bulletin 1998/24.

Ward, B. et al "NL Propogation Applied To Improvement of Resolution in Diagnostic Medical Ultrasound," J. Acoustic Soc. Amer 101(1) Jan. 1997 pp. 143–154.

Ward, B et al "Lateral Medical Ultrasound Scanners", 1995 World Congress on Ultrasonics pp. 965–968.

Deborah J. Rubens, M.D., "Sonoelasticity Imagaing of Prostate Cancer: In Virtro Results." Radiology, vol. 195, No. 2, 1995.

T.G. Leighton, "Transient excitation of insonated bubbles." Research Notes.

(List continued on next page.)

*Primary Examiner*—Francis J. Jaworski
*Attorney, Agent, or Firm*—Craig A. Summerfield; Brinks Hofer Gilson & Lione

[57] ABSTRACT

An ultrasound method and system are provided for producing three dimensional images. During an imaging session, a transducer, in response to a transmit beamformer, transmits ultrasonic energy at a first frequency band into a subject. The subject may be kept free of added ultrasound contrast agent throughout the entire imaging session. A receive beamformer receives ultrasonic echo information associated with the transmitted ultrasonic energy. Information signals associated with a second frequency band, such as a harmonic frequency band, are obtained from the echo information. A three-dimensional reconstruction is formed or a volume quantity is calculated in response to the information signals. The transmission of ultrasonic energy may also include energy focused along an elongated high power region or a line focus.

10 Claims, 9 Drawing Sheets

U.S. PATENT DOCUMENTS

| | | |
|---|---|---|
| 5,233,994 | 8/1993 | Shmulewitz . |
| 5,255,683 | 10/1993 | Monaghan . |
| 5,287,753 | 2/1994 | Routh et al. . |
| 5,305,756 | 4/1994 | Entrekin et al. . |
| 5,313,948 | 5/1994 | Murashita et al. . |
| 5,329,496 | 7/1994 | Smith . |
| 5,353,354 | 10/1994 | Keller et al. . |
| 5,358,466 | 10/1994 | Aida et al. . |
| 5,380,411 | 1/1995 | Schlief . |
| 5,386,830 | 2/1995 | Powers et al. . |
| 5,396,285 | 3/1995 | Hedberg et al. . |
| 5,398,691 | 3/1995 | Martin et al. . |
| 5,409,688 | 4/1995 | Quay . |
| 5,410,205 | 4/1995 | Gunuraja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,433,207 | 7/1995 | Pretlow, III . |
| 5,435,310 | 7/1995 | Sheehan et al. . |
| 5,435,311 | 7/1995 | Umemura et al. ................... 600/439 |
| 5,438,554 | 8/1995 | Seyed-Bolorforosh et al. . |
| 5,443,071 | 8/1995 | Banjanin et al. . |
| 5,454,371 | 10/1995 | Fenster et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,474,073 | 12/1995 | Schwartz et al. . |
| 5,479,926 | 1/1996 | Ustuner et al. . |
| 5,482,046 | 1/1996 | Deitrich . |
| 5,523,058 | 6/1996 | Umemura et al. . |
| 5,526,816 | 6/1996 | Arditi . |
| 5,540,909 | 7/1996 | Schutt . |
| 5,546,807 | 8/1996 | Oxaal et al. . |
| 5,558,092 | 9/1996 | Unger et al. . |
| 5,560,364 | 10/1996 | Porter . |
| 5,562,095 | 10/1996 | Downey et al. . |
| 5,562,096 | 10/1996 | Hossack et al. . |
| 5,568,811 | 10/1996 | Olstad ................................ 600/443 |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,623,928 | 4/1997 | Wright et al. . |
| 5,628,322 | 5/1997 | Mine . |
| 5,632,277 | 5/1997 | Chapman et al. . |
| 5,655,535 | 8/1997 | Friemel et al. . |
| 5,675,554 | 10/1997 | Cole et al. . |
| 5,678,554 | 10/1997 | Hossack et al. . |
| 5,685,308 | 11/1997 | Wright et al. . |
| 5,696,737 | 12/1997 | Hossack et al. . |
| 5,699,805 | 12/1997 | Seward et al. ..................... 600/463 |
| 5,724,976 | 3/1998 | Mine et al. . |

OTHER PUBLICATIONS

Erick J. Chen, et al., "Young's Modulus Measurements of Soft Tissues with Application to Elasticity Imaging." IEE Transactions on Ultrasonics, Ferroelectrics, and Frequency Control, vol. 43, No. 1, Jan. 1996.

Pi Hsien Chang, et al, "Second Harmonic Imaging and Harmonic Doppler Measurements with Albunex." IEEE Transactions on Ultrasonics, Ferroelectrics, and Frequency Control, vol. 42, No. 6, Nov. 1996.

Marc Gensane, "Bubble population measurements with a parametric array." 1994 Accoustical Society of America, 95 (6) Jun.

Ken Ishihara et al., "new Approach to Noninvasive Manametry Baased on Pressure Dependent Resonant Shift of Elastic Microcapsules in Ultrasonic Frequency Characteristics." Japanese J. of Applied Physics, vol. 2 (1988).

Shmuel Gottlieb, M.D. et al., "Effect of Presure on Echocardiographic Videodensity from Sonicated Albumin: An In Vitro Model." J. Ultrasound Med. 14 (1995).

J.W. Norris, "The non–linear oscillation of a radially symmetric bubble in a time periodic pressure field." Dynamics and Stability of Systems, vol. 9, No. 1 (1994).

Michael S. Longuet–Higgins, Resonance in nonlinear bubble oscillations. J. Fluid Mech. (1991) vol. 24.

Chiang C. Mei, et al., "Parametric resonance of a spherical bubble." J. Fluid Mech. (1991) vol. 229.

V.L. Newhouse, et al., "Bubble size measurements using the nonlinear mixing of two frequencies." J. Acoust. Soc. Am. 75 (5), May 1984.

Janet B. Jones–Oliveira, et al., "Transient fluid—solid interaciton of submerged spherical shells revisited: Proliferation of frequencies and acoustic radiation effects." Acoustical Society of America, 96(2) Pt. 1, Aug. 1994.

Chandra M. Sehgal, PhD., et al., "Sonographic Engancement of Renal Cortex by Contrast Media." J. Ultrasound Med., 14 (1995).

William Armstrong et al., "Position Paper on Contrast Echocardiography", Am. Soc. Of Echocardiography, Jun. 6, 1994.

Fred Lee, Jr., M.D., "Sonoelasticity Imaging Results in in Vitro Tissue Specimins." Radiology, vol. 181, No. 1 Oct. 1991.

Kevin J. Parker, PhD. Et al., "Sonoelasticity of Organs: Shear Waves Ring a Bell". J. Ultrasound Med. 11 (1992).

Nico de Jong, "Physical properties and technical aspect of ultrasoind contrast agenst." (one page).

Robert M. Lerner, et al., "Sonoelasticity Images Derived from Ultrasound Signals in Mechanically Vibrated Tissues." Ultrasound in Med. And Biol., vol. 16, No. 3, 1990.

J. Ophir, et al., "Elastography: A Quantitative Method for Imaging the Elasticity of Biological Tissues." Ultrasonic Imaging 13, (1991).

J.A. Hossack, et al., "Improving transducer performance using multiple active layers." SPIE vol. 1733 (1992).

Volkmar Uhlendorf, et al., "Nonlinear Acoustical Response of Coated Microbubbles in Diagnostic Ultrasound." IEEE 1994 Ultrasonics Symposium.

John A. Hossack, et al., "Improving the Characteristics of a Transducer Using Multiple Piezoelectric Layers," IEEE Transactions on Ultrasonics, Ferroelectrics, and Frequency Control, vol. 40, No. 2, Mar. 1993.

"HP Ultrasound Technologies—Viability." About HP Ultrasound Imaging, WWW document 1997.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the Americal College of Cardiology." American College of Cardiology. 45th Annual Scientific Session, Mar. 24–27, 1996 pp. 21A, 63A, 239–240A.

Yang–Sub Lee et al., "Timd–domain modeling of pulsed finite–amplitude sound beams." J. Acoustical Society of America, 97 (2), Feb. 1995.

Michalakis A. Averkiou, et al. "Self–demodulation of amplitude and frequency. Modulated pulses in a thermouisceus fluid." J. Acoustical Society of America, vol. 94, No. 5, Nov. 1993.

Kotaro Sato, et al., "Numerical analysis of a gas bubble near a rigid boundary in an oscillatory pressure field." J. Acoustical Society of America, 93 (4), Apr. 1993.

L.W. Anson et la., "Ultrasonic scattering from sperical shells including viscous and thermal effects." J. Acoustical Society of America, 93 (4), Apr. 1993.

K.J. Parker, et al., "Tissue Response to Mechanical Vibrations for 'Sonoelasticity Imaging'." Ultrasound in Med. & Biol., vol. 16, No. 3, (1990).

B. Schrope, et al., "Simulated Capillary Blood Flow Measurement Using A Nonlinear Ultrasonic Contrast Agent," Ultrasonic Imaging 14 (1992).

H. Edward Karrer, eet al., "A Phased Array Acoustic Imaging System for Medical Use." 1980 Ultrasonics Symposium.

"Small Spheres Lead to Big Ideas." Research News, Science vol. 267, Jan. 20, 1995.

Excerpt from Ultrasonics: Fundamentals and Applications (1992), pp. 380–393, 363–365.

Abstracts Journal of the Americal Society of Echocardiography, Abstract Sessions IV and Poster Session A, vol. 8, No. 3 pp. 345–346, 355, 358–364.

Chandra M. Seghal, PhD, et al., "Influence of Postprocessing Curves on Contrast—Echographic Imaging: Preliminary Studies." J. Ultrasound Med., 14 (1995).

Dan Sapoznikov, et al., "Left Ventricular Shape, Wall Thickness And Function Based On Three–Dimensional Reconstruction Echocardiography." Dept of Cardiology, Hadasah University Hospital, Jerusalem, Isreal.

C.B. Buckhardt, et al., "Ultrasound Axicon: device for focusing over a large depth." The Journal of the Acoustical Society of America, vol. 54, No. 6, (1973).

Olaf T. von Ramm, et al., "Real Time Volumetric Ultrasound Imaging System." Journal of Digital Imaging, vol. 3, No. 4 (Nov.), 1990 pp. 261–266.

Shinichi Tamura et al., "Three–Dimensional Reconstruction of Echocardiograms Based on Orthogonal Sections." Pattern Recognition vol. 18, No. 2 pp. 115, 124 (1985).

Hugh A. McGann, et al., "Multidimensional Ultrasonic Imaging For Cardiology." Proceedings of the IEEE, vol. 76, No. 9, Sep. (1988).

William E. Lorensen, et al., "Marching Cubes: A High Resolution 3D Surface Construction Algorithm." Computer Graphics, vol. 21, Nov. 4, Jul. (1987).

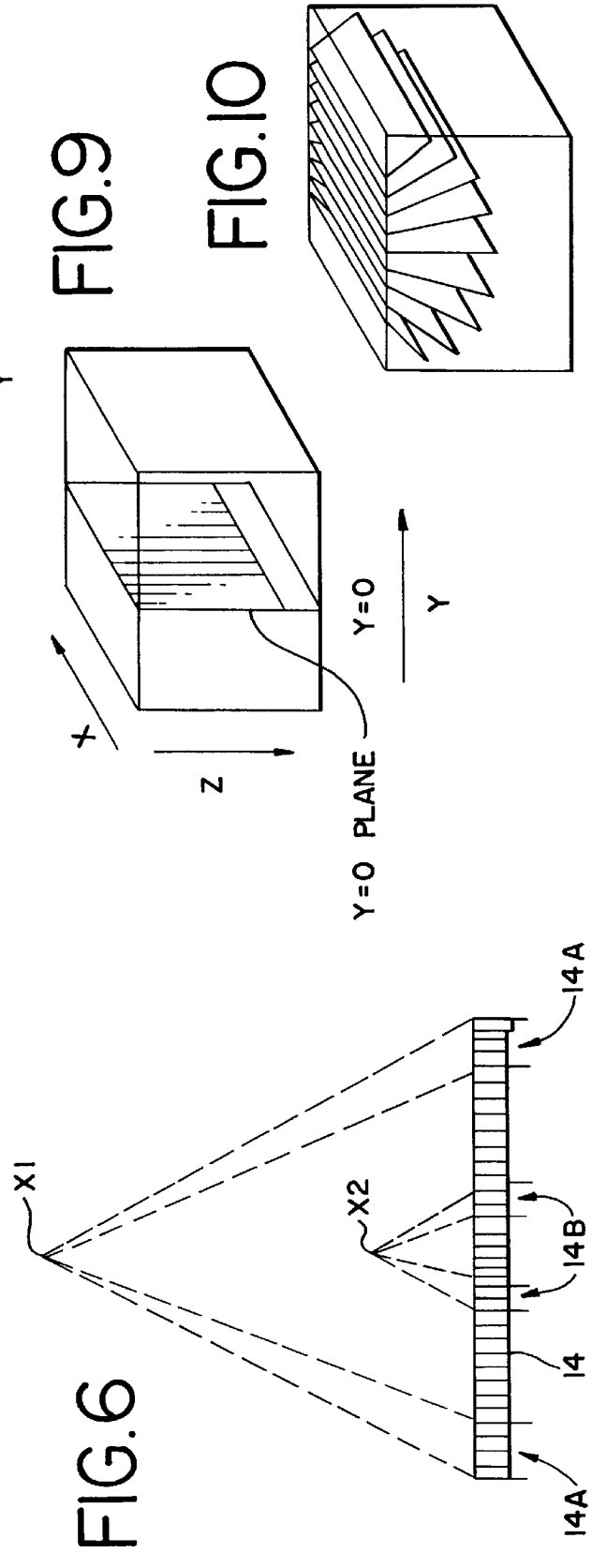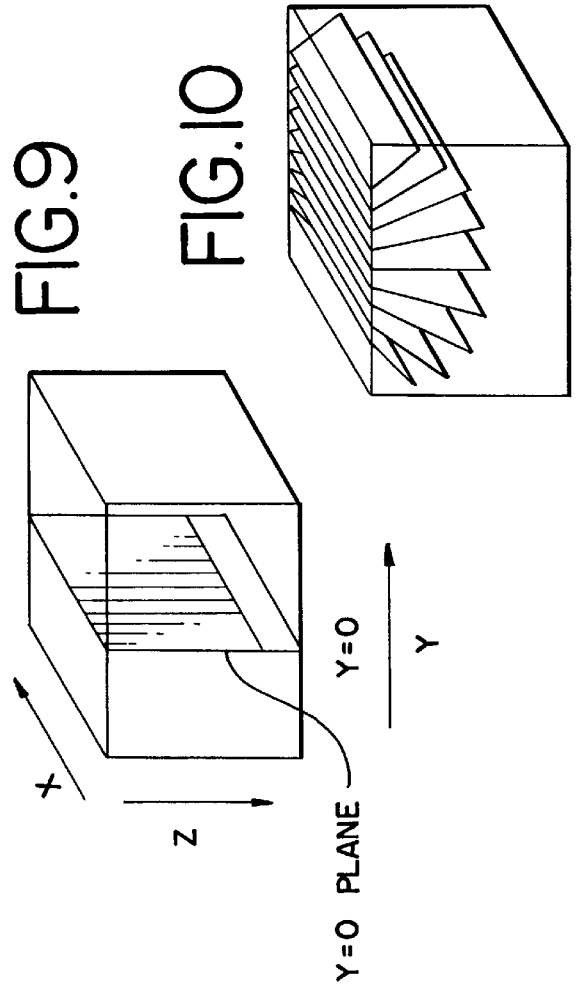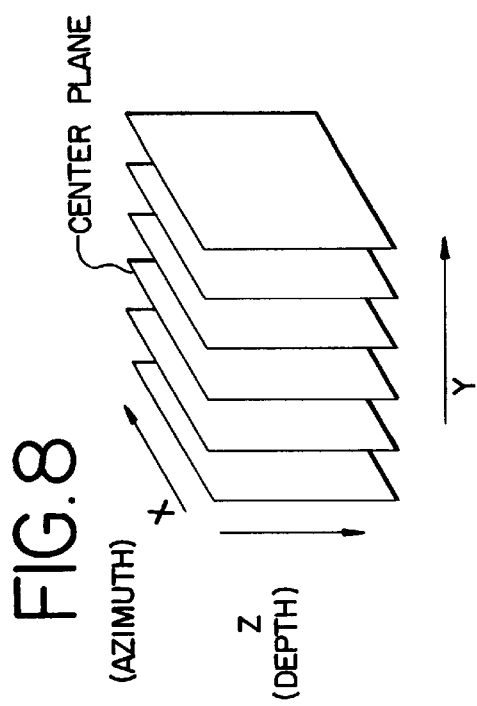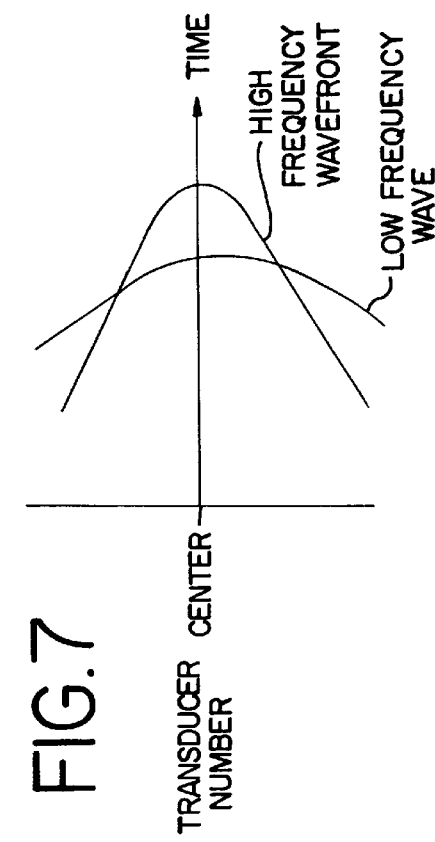

FIG. 13
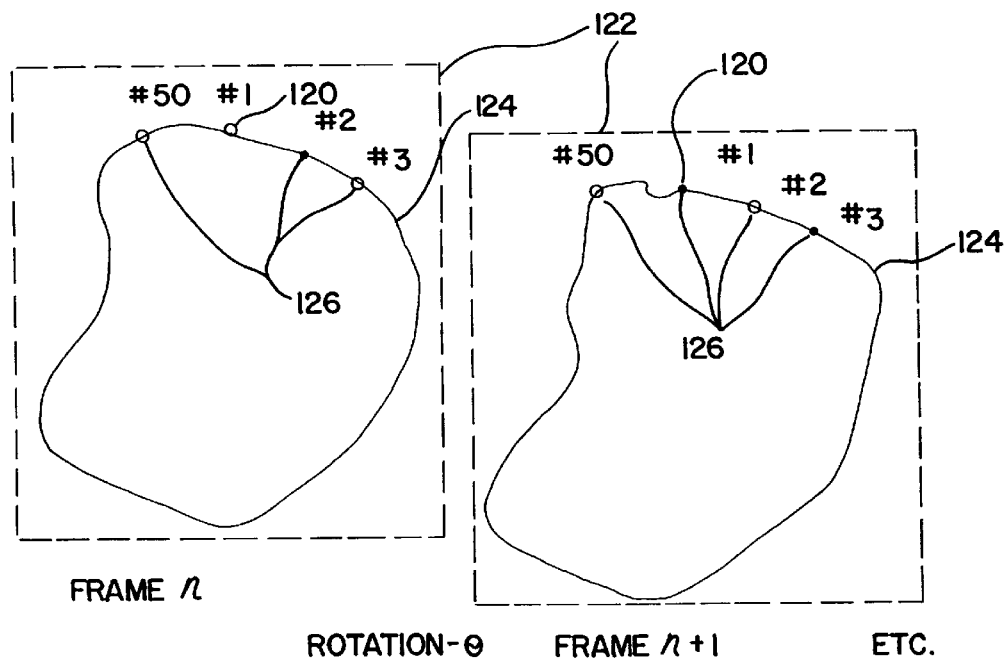
FRAME $n$  
ROTATION-$\theta$    FRAME $n+1$    ETC.
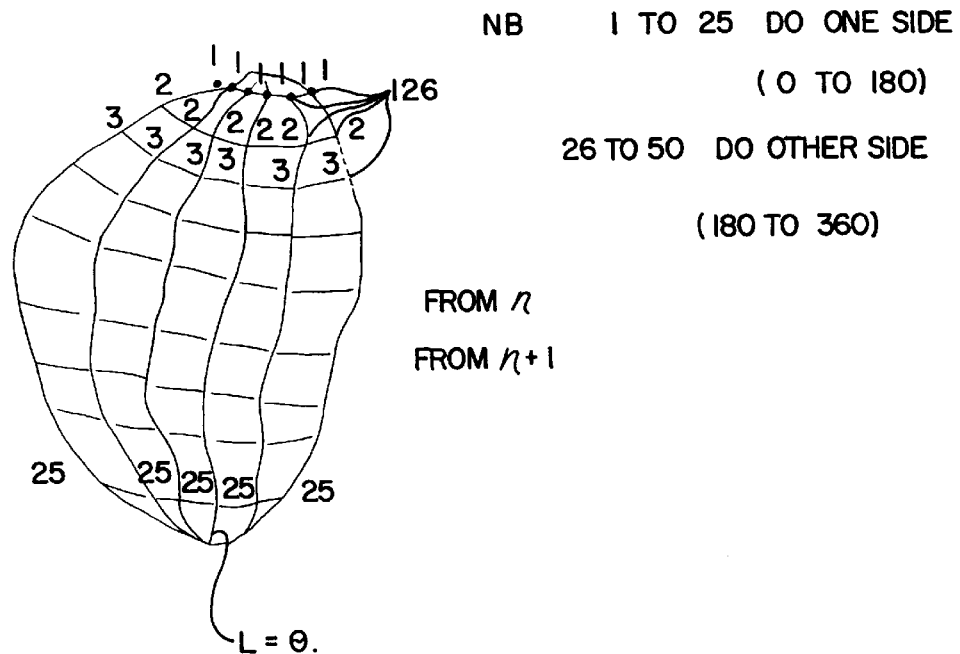
NB    1 TO 25    DO ONE SIDE  
                 (0 TO 180)  
     26 TO 50    DO OTHER SIDE  
                 (180 TO 360)
FROM $n$  
FROM $n+1$

FIG.14
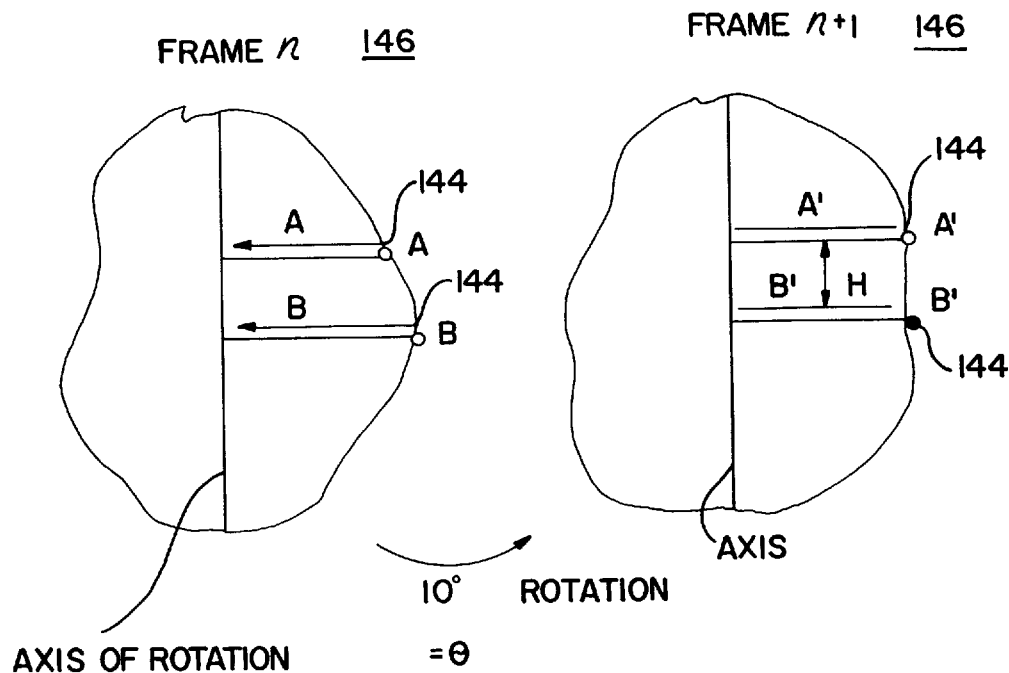
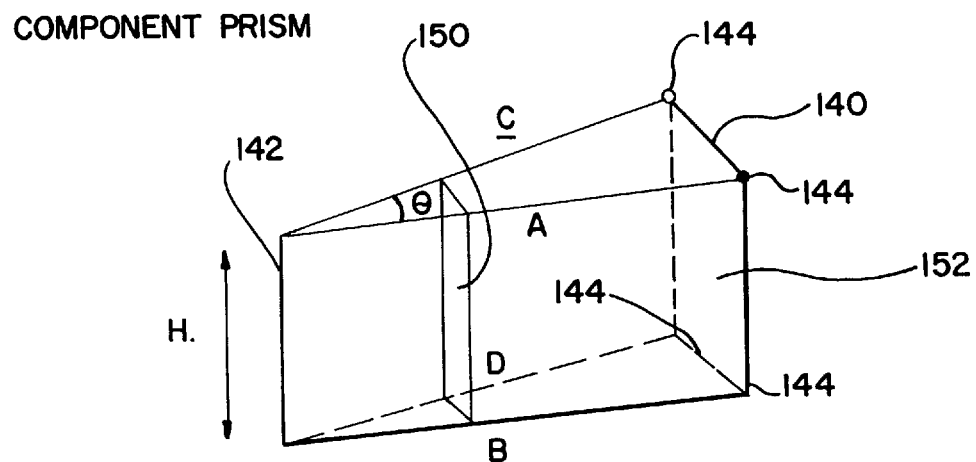

ULTRASONIC SYSTEM AND METHOD FOR HARMONIC IMAGING IN THREE DIMENSIONS

This application is a division of application Ser. No. 08/924,407, filed Aug. 22, 1997, (pending).

BACKGROUND OF THE INVENTION

This invention relates to an ultrasound system and method for generating a three dimensional representation and for quantifying as a function of volume.

There is growing interest in three-dimensional ultrasonic imaging, such as three dimensional ultrasound contrast agent imaging. To generate the three-dimensional image, volumetrically spaced information, such as planar or line information, associated with positional information is obtained by using any of various transducers.

One approach is to use a two-dimensional transducer array to obtain three-dimensional image information directly. A two-dimensional array can be used to scan electronically in any desired orientation to acquire the desired information. Another approach is to collect multiple two-dimensional image data frames using a one-dimensional transducer array along with relative positional information among the image data frames so that these frames may be subsequently assembled in a three-dimensional volume to form the desired three-dimensional reconstruction.

Based on echo signals received from the transducer, the volumetric information, such as planar image information, is generated. The image information is derived as a function of various imaging modes. For example, B-mode or Color Doppler image information is generated.

Once the volumetrically spaced information, such as planar image information, and associated positional information is provided, standard methods are employed for assembling the image information into a three-dimensional volume of the subject and for providing an appropriate display such as a cross section, a surface rendering, or the like.

SUMMARY OF THE INVENTION

The various aspects of this invention provide for potentially better resolution and less clutter. Furthermore, by suppressing the harmonic content of the excitation signal, the benefits of harmonic imaging of tissue may be increased.

According to a first aspect of this invention, an ultrasound method and system are provided for producing three dimensional images. During an imaging session, a transducer, in response to a transmit beamformer, transmits ultrasonic energy at a first frequency band into a subject. The subject is kept free of added ultrasound contrast agent throughout the entire imaging session. A receive beamformer receives ultrasonic echo information associated with the transmitted ultrasonic energy. Information signals associated with a second frequency band, such as a harmonic frequency band, are obtained from the echo information. A three-dimensional reconstruction is formed in response to the information signals.

According to a second aspect of this invention, the transmit and receive processes discussed above are used to calculate a volume quantity. The volume quantity is displayed with or without generating the three-dimensional reconstruction.

According to a third aspect of this invention, the transmit process includes transmitting ultrasonic energy in power bursts into a subject, where each power burst comprises a first center frequency and a respective envelope shape. Each envelope shape rises gradually to a respective maximum value and falls gradually from the respective maximum value. The transmissions occur with or without contrast agents being provided in the subject. Based on the information signals obtained from received echo signals, an image representing three-dimensions is displayed.

According to a fourth aspect of this invention, the ultrasonic energy is transmitted at a fundamental frequency into a subject in a transmit beam having an elongated high power region. The elongated region is formed by focusing at least first selected frequency components from at least selected transducer elements at a first range and focusing at least second frequency components from at least selected transducer elements at a second range. A three-dimensional reconstruction is formed from information signals associated with harmonics of the fundamental frequency band.

According to a fifth aspect of this invention, a line focus for the transmit beam is used. A three-dimensional reconstruction is formed from information signals associated with harmonics of the transmitted fundamental frequency band.

Further aspects and advantages of the invention are discussed below in conjunction with the preferred embodiments.

BRIEF DESCRIPTION OF THE DRAWINGS

FIG. 6 is a schematic representation of a compound focus arrangement.

FIG. 7 is a graph showing high and low frequency wavefronts.

FIGS. 8, 9 and 10 are three schematic perspective views showing a manner in which multiple image data frames can be registered with respect to one another in three-dimensions to form a three-dimensional representation.

FIG. 13 is a schematic representation for generating a three dimensional polygon mesh.

FIG. 14 is a schematic representation for calculating a volume from data representing three-dimensions.

DETAILED DESCRIPTION OF PREFERRED EMBODIMENTS

Figure 1:
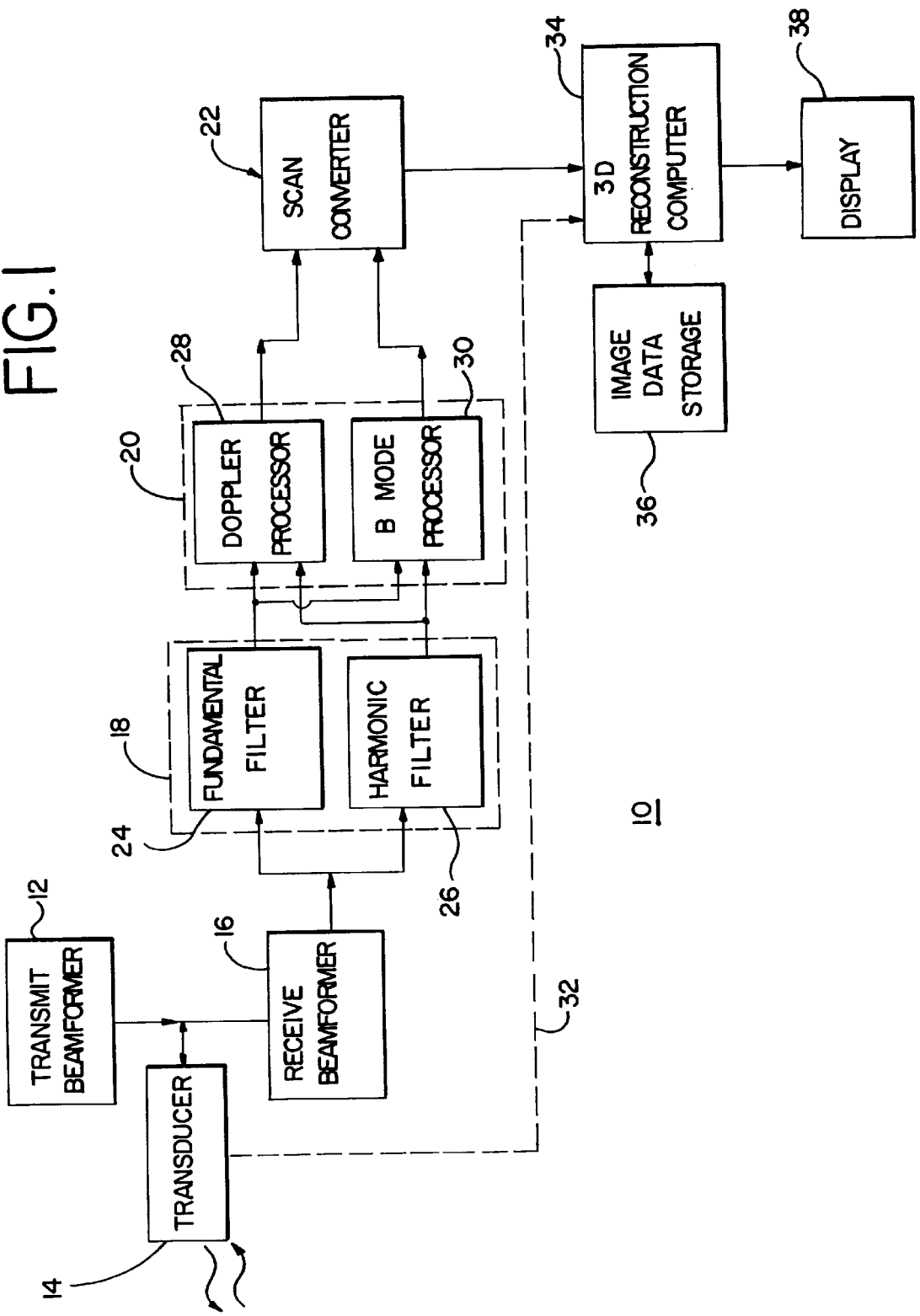
FIG. 1 is a block diagram of an ultrasound system for acquiring harmonic and fundamental frequency data for three-dimensional imaging.

The preferred embodiments described below are designed to reduce the effects of noise in three-dimensional reconstruction. The effects of noise are reduced by tissue harmonic imaging and reduced transmission of harmonic information. The preferred embodiments are also designed to generate a three-dimensional image with better resolution than three-dimensional imaging of contrast agents.

Three Dimensional and Harmonic Overview

Four methods for acquiring data for three-dimensional imaging are described below, though other methods may be used. First, a single element transducer (or an axially focused annular array) is mechanically scanned so as to sweep a volume or three-dimensional space. An example of this first method is the method practiced for the Medison-Kretz Combison 530 (Korea). Moving parts for sweeping the volume are enclosed in a fluid filled housing. Thus, the three-dimensional space is swept by mechanically moving the transducer over two-dimensions.

The second method is to use a two-dimensional transducer array to obtain three-dimensional image information directly. A two-dimensional array can be used to scan electronically in any desired orientation to acquire the desired information. Typically, the two-dimensional array is sub-sampled. It is generally impractical to provide a fully sampled 2D array (e.g. 64×64 is 4096 elements). An example of a two-dimensional array is disclosed in U.S. Pat. No. 5,329,496 (Smith). An imaging system for use with the disclosed array is described in U.S. Pat. No. 5,546,807 (Oxaal et al.).

The third method is to collect multiple two-dimensional image data frames associated with relative positional information using a one-dimensional transducer array. The two-dimensional image data frames or image planes are non-coplanar, such as two or more rotationally offset planes or two or more planes offset in elevational position. The positional information provides the relative position among the image data frames so that these frames may be subsequently assembled in a three-dimensional volume to form the desired three-dimensional reconstruction. One dimension is electronically scanned and another dimension is mechanically scanned by rotation, translation, or any combination thereof. For example, the transducer is swept. Sweeping corresponds to rotating the transducer about an axis along the azimuth of the lens surface.

One approach for this third method is to use manual motion detection techniques based on analysis of ultrasonic images. See Tamura et al., "Three-Dimensional Reconstruction of Echocardiograms Based on Orthogonal Sections" (Pattern Recognition, 18, 2, pp. 115–124, 1985).

Another approach is to sense position based on image motion detection, such as disclosed in MULTIPLE ULTRASOUND IMAGE REGISTRATION SYSTEM, METHOD AND TRANSDUCER, U.S. application Ser. Nos. 08/621,561 (filed Mar. 25, 1996 and now abandoned), 08/807,498 (filed Feb. 27, 1997 and now abandoned) and unassigned (filed herewith: Atty. Ref. No. 5050/204) to Hossack et al., assigned to the assignee of the present invention, and the disclosures of which are herein incorporated by reference. See also U.S. Pat. No. 5,127,409 to Daigle. The position information is calculated from scan data.

Schwartz U.S. Pat. No. 5,474,073 describes a qualitative three-dimensional method using a hand-held transducer array and an assumed scan motion. The transducer is moved manually by free hand motion. The spacing between each two-dimensional image is assumed to be equal.

Keller U.S. Pat. No. 5,353,354 discloses a transducer array equipped with accelerometers or magnetic sensors designed to measure the position and orientation of the transducer, and, therefore, relative motion between respective image planes. The free hand movement of the transducer is monitored. Suitable magnetic positioning sensors are described in U.S. Pat. Nos. 4,945,305 and 4,849,692 to Blood. Preferably, a pulsed DC type position sensor is used for this type of transducer. Such systems include the mini Bird™ and Flock of Birds™ systems by Ascension Technology Corp. of Burlington, Vt. Alternatively, the 3Space Fastrak from Polhemus (Colchester, Vt.) is used. This device is less susceptible to interference from ferrous objects.

Mechanical manipulation guides or fixtures capable of rotation, translation, or a fan-like sweep may also be used to spatially orient each two-dimensional image plane. Such devices are disclosed in U.S. Pat. Nos. 5,454,371 (Fenster) and 5,562,095 (Downey et al.).

Another approach is to provide a spaced arrangement of LEDs, such as infra-red LEDs, on the transducer. The LEDs arc activated in sequence and monitored with a camera. The position and orientation is then inferred from an image of the LEDs generated by the camera. One such device is manufactured by Surgical Navigation Technologies of Broomfield, Colo.

Still another approach is to use a spaced arrangement of microphones. See King U.S. Pat. No. 4,100,916. The position information is determined from the time of flight of acoustic impulses generated by a source on the transducer to the various microphones.

Yet another approach is to use a motorized array to collect the desired set of image data frames by precisely controlling the movement of the transducer array. One example is the Acuson V5M Transesophageal transducer, a rotating transducer. The rotating transducer produces two-dimensional images at known angles of rotation. A lens design for such a transducer is shown in U.S. Pat. No. 5,562,096 (Hossack, et al., assigned to the assignee of the present invention). Another example is a transthoracic transducer, such as disclosed in Pini U.S. Pat. No. 5,159,931. See also, Sapoznikov et al., "Left Ventricular Shape, Wall Thickness and Function Based on Three-Dimensional Reconstruction Echocardiography" ("Computers in Cardiology," IEEE Computer Society Press, Cat CH 2476-0, pp. 495–498, 1987). A related approach is to use a large rotating transducer as described in McCann et al., "Multidimensional Ultrasonic Imaging for Cardiology" (Proceedings of IEEE, 76, 9, pp. 1063–1072, Sept. 1988). For example and preferably for use with harmonic imaging, an Acuson 3V2c transducer is placed in a rotatable fixture, such as disclosed in Pini or McCann.

The fourth method uses a single element transducer rotatable in one-dimension, a linear array unfocused (defocused) in the elevational direction (such as by a concave lens with a len velocity less than that of tissue) or a two-dimensional array to scan a volume. As disclosed in U.S. Pat. No. 5,305,756 to Entrekin et al., a fan shaped beam focused in the azimuthal direction and divergent in the elevational direction is used to scan orthogonal to the longitudinal face of the transducer or in a sector axial to the transducer. By using known two-dimensional processing, each range sample corresponds to a summation or integration of various elevational positions corresponding to that range at a plurality of elevational positions in the fan shaped beam. A plurality of range samples corresponding to each line in the axial scan pattern is obtained. A two dimensional image is generated as known in the art from the range samples (corresponding to integrated samples). The two dimensional image is a reconstruction of data representing a volume or three dimensions.

Any of the various methods discussed above are used to generate a three-dimensional image in accordance with this invention. The three-dimensional image is based on receiving signals at a harmonic frequency band associated with a fundamental transmit frequency band. Harmonic frequencies are frequencies associated with non-linear propagation or scattering of transmit signals. As used herein, harmonic includes subharmonics as well as second, third, fourth, and other higher harmonics. Fundamental frequencies are frequencies corresponding to linear propagation and scattering of transmit signals or the first harmonic. Non-linear propagation or scattering corresponds to shifting energy associated with a frequency or frequencies to another frequency or frequencies. The harmonic frequency band may overlap the fundamental frequency band.

In tissue harmonic imaging, no additional non-linear contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no nonlinear contrast agent is introduced into the tissue at any time during the imaging session.

It has been observed that tissue harmonic images provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than would a transmit beam formed using signals transmitted directly at the second harmonic.

The harmonic imaging technique described above can be used for both tissue and contrast agent harmonic imaging. In contrast agent harmonic imaging, any one of a number of well known nonlinear ultrasound contrast agents, such as micro-spheres or the FS069 agent by Schering of Germany, is added to the target or subject in order to enhance the non-linear response of the tissue or fluid. The contrast agents radiate ultrasonic energy at harmonics of an insonifying energy at fundamental frequencies. However, contrast agents may require unnecessary procedures for three-dimensional imaging.

Since the harmonic imaging techniques described above can be used for both tissue and contrast agent harmonic imaging, it should be understood that the introduction of an added nonlinear contrast agent into the tissue being imaged is not implied in any of the following claims unless such added non-linear contrast agent is expressly recited.

The Ultrasound System and Waveform Generation

Referring now to the figures, and in particular, FIG. 1, an ultrasound system is generally shown at 10. The ultrasound system 10 includes a transmit beamformer 12, a transducer 14, a receive beamformer 16, a filter block 18, a signal processor 20, and a scan converter 22. The ultrasound system 10 is configurable to acquire information corresponding to a plurality of two-dimensional representations or image planes of a subject for three-dimensional reconstruction. Other methods, such as those associated with a two dimensional or single element transducer array, may be used. To generate each of the plurality of two-dimensional representations of the subject during an imaging session, the ultrasound system 10 is configured to transmit, receive and process during a plurality of transmit events. Each transmit event corresponds to firing an ultrasound scan line into the subject.

For each or a plurality of transmit events, control signals are provided to the transmit beamformer 12 and the receive beamformer 16. The transmit beamformer 12 is caused to fire one or more acoustic lines in each transmit event, and the receive beamformer 16 is caused to generate in phase and quadrature (I and Q) information along one or more scan lines. Alternatively, real value signals may be generated. A complete frame of I and Q information corresponding to a two-dimensional representation (a plurality of scan lines) is preferably acquired before I and Q information for the next frame is acquired.

The transmit beamformer 12 is of a construction known in the art, such as a digital or analog based beamformer capable of generating signals at different frequencies. The transmit beamformer 12 generates one or more excitation signals. Each excitation signal has an associated center frequency. As used herein, the center frequency represents the frequency in a band of frequencies approximately corresponding to the center of the amplitude distribution. Preferably, the center frequency of the excitation signals is within the 1 to 15 MHz range, such as 2 MHz, and accounts for the frequency response of the transducer 14. The excitation signals preferably have non-zero bandwidth.

Figure 2:
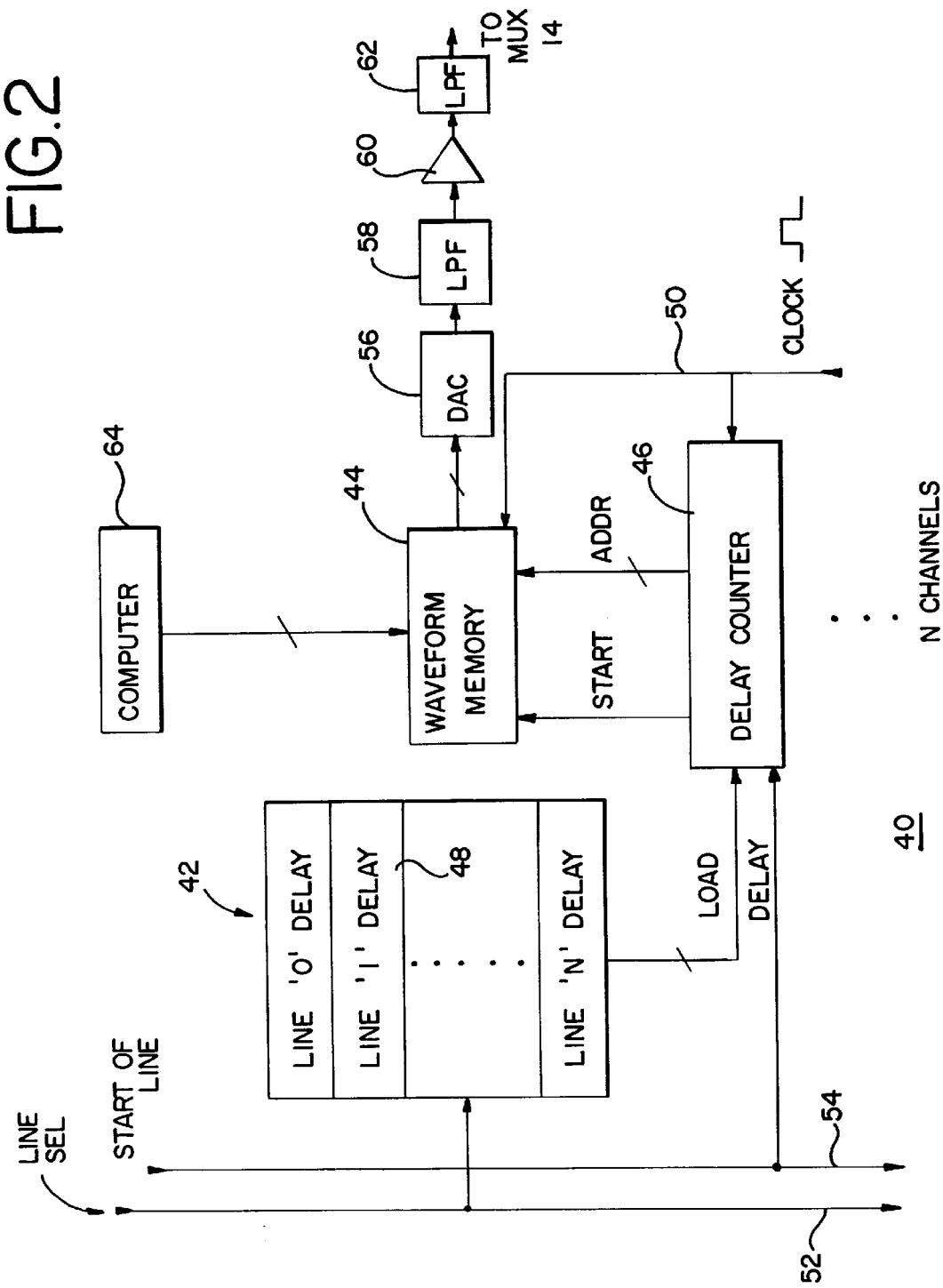
FIG. 2 is a block diagram of a transmit beamformer suitable for use in the system of FIG. 1.

Turning now to FIG. 2, this figure shows a block diagram of a first preferred embodiment 40 of the transmit beamformer of FIG. 1. As shown in FIG. 2, the transmit beamformer 40 includes N channels, one for each of the transducer elements of the transducer 14 (FIG. 1). Each channel includes a delay memory 42, a waveform memory 44, and a delay counter 46 (FIG. 2). The delay memory 42 includes m words 48, such as 256 words 48, one word 48 for each possible steering angle or ultrasound transmit scan line. For ultrasound transmit lines associated with a plurality of focus regions, each delay word 48 corresponds to the ultrasound transmit line and the focal region. As known in the art, the ultrasonic beams or scan lines are focused in one of various formats, such as linear, steered linear, sector, or Vector®. The ultrasonic waves are focused using various delay and apodization techniques. Each word 48 of the delay memory 42 is set equal to a negative number equal to the number of clock cycles on the clock signal line 50 that elapse between a start of line signal on line 54 and the first non-zero value of the associated waveform. For simplicity, it is assumed that zero is defined as a word 48 having the most significant bit equal to one and all other bits equal to zero. Hence, the most significant bit becomes an enable signal for the waveform memory 44.

The waveform memory 44 in this embodiment stores a single waveform in digital form, which is used for all transmit scan lines. The waveform memory 44 includes, for example, 64 or 128 successive 8 bit words. The magnitude of each 8 bit word corresponds to the voltage amplitude at the respective position in the waveform. When the waveform memory 44 is read with a 40 MHz clock on the line 50, the resulting sequence of digital values defines a waveform approximately 1.6 to 3.2 microseconds in duration.

The delay memory 42 is not required, but it reduces memory requirements for the waveform memory 44. This is because the delay memory 42 eliminates the need to store a large number of leading zeros when the ultrasound line is steered at a large angle or to have different start of transmit signals for each channel.

In use, each channel responds to a scan line selection signal on line 52 by loading the word 48 for the selected scan line or line and focal region into the delay counter 46. The delay counter 46 responds to a start of scan line signal on line 54 by incrementing the stored value with each cycle of the 40 MHz clock on line 50. When the counter 46 increments to zero, it enables the waveform memory 44. Subsequently generated values of the counter 46 (incrementing now from zero upwards) become address values for the waveform memory 44. As each word of the waveform memory 44 is addressed, the corresponding 8 bit word is read and applied to a digital to analog converter 56.

The analog output signal of the converter 56 is passed through a low pass filter, such as a Bessel filter 58, to reduce sampling effects and then to an amplifier 60. The output of the amplifier 60 can be passed through an additional low pass filter 62 to improve harmonic rejection. The output of the low pass filter 62 is the excitation signal discussed above that is applied to the respective transducer element of the transducer 14 (FIG. 1). The low pass filters 58, 62 preferably provide a sharp cut-off with a low stop band level in order to substantially eliminate ultrasonic energy in the transmitted pulse at the harmonic frequency.

Waveform Shaping

The transmit beamformer 40 utilizes values for the waveforms stored in the waveform memory 44 and the delays stored in the delay memory 42 that enhance insonification of the nonlinear contrast agent or tissue in the subject. In order to enhance the harmonic image, it is preferred to shape the waveform in the frequency domain such that substantially no harmonic energy is transmitted. Other than the filtering discussed above, this can be done using a suitably programmed transmit beamformer as described in U.S. application Ser. No. 08/771,345, filed Dec. 16, 1996 and now U.S. Pat. No. 5,696,737 and assigned to the assignee of the present inventions or a suitably filtered or otherwise designed system as described in U.S. application Ser. Nos. 08/893,271, 08/893,237 now U.S. Pat. No. 5,833,614, filed Jul. 15, 1997.

Figure 3:
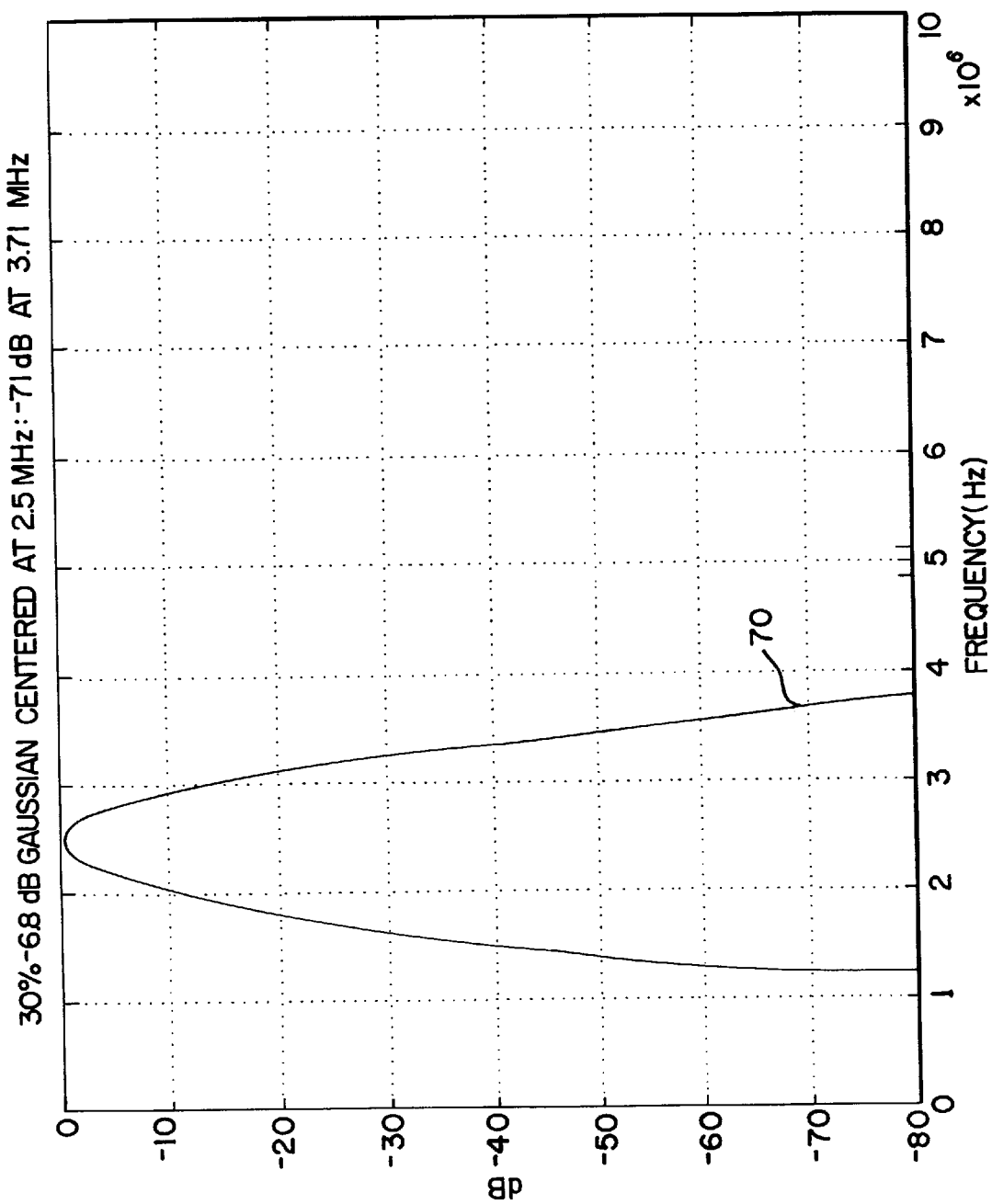
FIG. 3 is a graph of a Gaussian pulse in the frequency domain.

The waveform stored in the waveform memory 44 is shaped to suppress ultrasonic energy in a wide pass band centered in the harmonic frequency band. For example, the spectrum of the desired pulse can be designed on a computer 64. FIG. 3 shows the frequency spectrum of one suitable pulse 70 which is centered at the fundamental frequency of 2.5 MHz and is generally Gaussian in shape. The particular Gaussian shape shown in FIG. 3 has an amplitude reduced by 71 dB at 3.71 MHz. The bandwidth of the pulse 70 is 30% of the center frequency, measured at points −6.8 dB with respect to the peak amplitude. Note that the pulse 70 has substantially no energy at 5 MHz, the first harmonic of the fundamental center frequency. This invention is not limited to use with Gaussian pulses, and a wide range of spectra can be used, such as spectra associated with pulses generated at lower sample rates per cycle.

Figure 4:
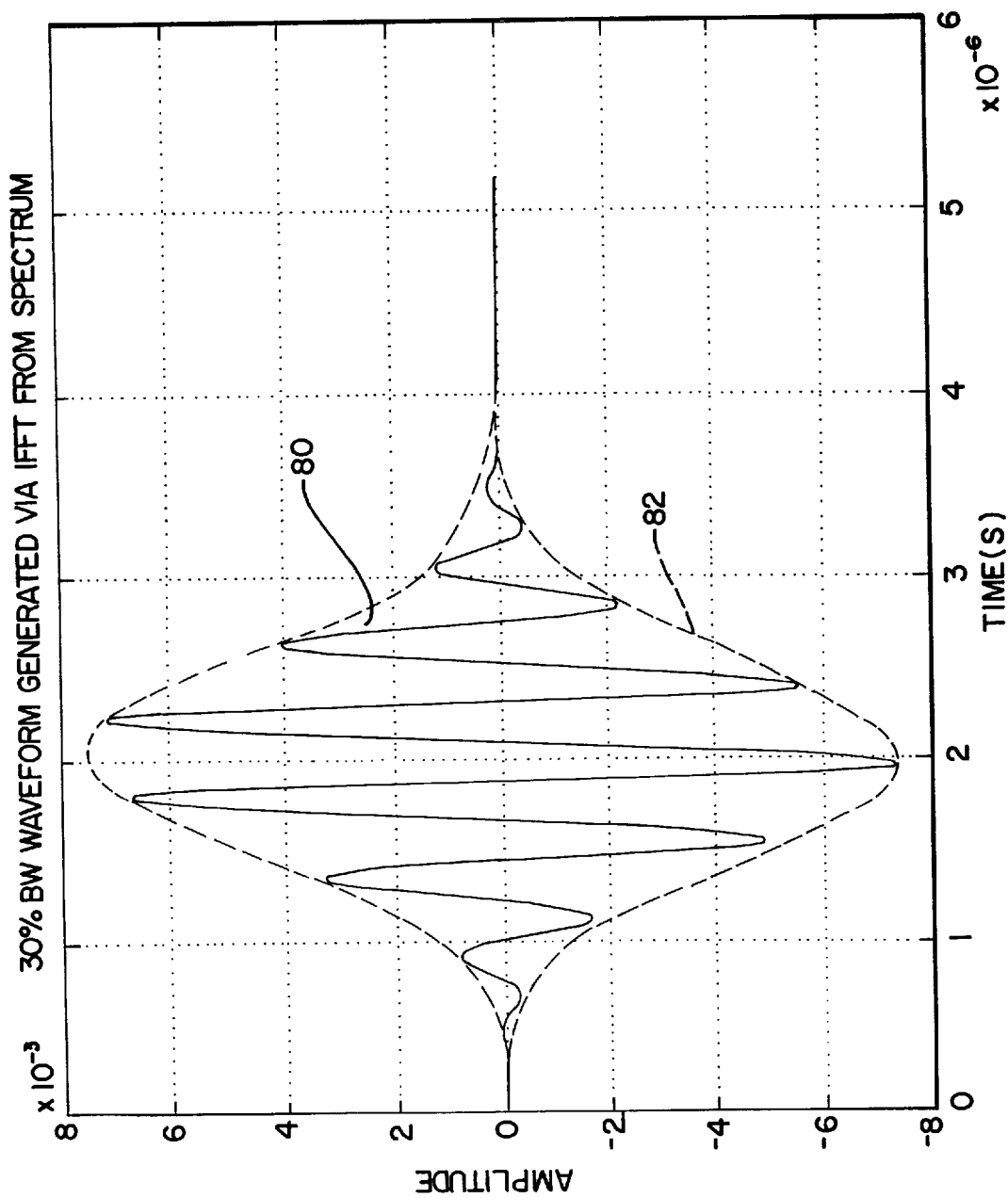
FIG. 4 is a graph of a waveform in the time domain corresponding to the Gaussian pulse of FIG. 3.

Once the desired pulse has been designed, an inverse fast Fourier transform is then performed to generate the corresponding time domain waveform. FIG. 4 shows a waveform 80 which corresponds to the pulse 70 of FIG. 3. Note that the waveform 80 includes an oscillating component having a frequency of about 2.5 MHz. This oscillating component is shaped by an envelope 82. The envelope 82 rises gradually from zero amplitude to a maximum amplitude, and then falls gradually from the maximum amplitude back to zero amplitude. Thus, the envelope 82 is quite different from the envelope for a switched pulse train, which is substantially rectangular in shape. The gradually increasing and gradually decreasing envelope 82 of FIG. 4 brings with it the advantage of reduced ultrasonic energy at harmonics of the fundamental frequency.

Once a waveform such as the waveform 80 of FIG. 4 has been designed, the waveform 80 can be coded into binary samples at a suitable sample rate and then stored in the waveform memory 44 (FIG. 2). The waveform memory 44 may be a read only memory, in which case the computer 64 may not be required to be connected to the transmit beamformer 40. Alternately, the waveform memory 44 may be a volatile memory which is programmed at power-up initialization by the computer 64. The computer 64 may perform any desired subset of the pulse designing steps described above. Typically, the desired pulse may be one of several selectable pulses included in a menu for user choice.

When the waveform in the waveform memory 44 is designed as described above the result is a broad band waveform in the waveform memory 44 which simultaneously has substantially no radiated energy in a broad band centered oil the harmonic. In the example of FIGS. 3 and 4, substantially no ultrasonic energy is radiated at frequencies above 4 MHz, or in a bandwidth of ±1 MHz with respect to the second harmonic (5 MHz). Preferably, the energy component at the second harmonic band is more than 30 dB reduced over a finite bandwidth with respect to the magnitude of the fundamental frequency. The finite bandwidth is greater than or equal to 5% of the harmonic of the fundamental center frequency. Ideally, the energy component of the second harmonic band is more than 40 dB or 50 dB reduced with respect to the peak amplitude over a bandwidth greater than or equal to 15% of the harmonic of the fundamental center frequency.

Of course, it is not necessary to define the waveform 80 initially in the frequency domain. A Gaussian pulse can be defined in the time domain. Furthermore, the envelope need not be Gaussian; it may be some other window function such as a Hamming pulse, a modified Gaussian pulse, or any other suitable pulse. In some applications it may be preferable to use a narrow bandwidth pulse and thereby achieve a very high reduction of energy at the harmonic, since the harmonic of the lower bandedge is well above the upper bandedge. On other occasions it may be preferable to use a wider bandwidth pulse, for example, to obtain better axial (temporal) resolution. In this case, somewhat reduced reduction of energy at the harmonic may be accepted. Techniques for suppressing the harmonic content of the transmit signal and alternative embodiments are discussed in ULTRASONIC HARMONIC IMAGING SYSTEM AND METHOD, U.S. application Ser. No. 08/893,288 assigned to the assignee of the present invention, the disclosure of which is herein incorporated by reference.

In addition to suppressing the harmonic content of the transmit signal, optimum imaging is obtained when the transmit beam insonifies the subject and any ultrasound contrast agents at power levels within a desired range. Power levels below this range may not be sufficiently high to cause tissues in the subject or the ultrasound contrast agent to radiate at the harmonic frequency. Power levels above this range may destroy any contrast agent prematurely. Additionally, since there are FDA limits on ultrasound intensity, a sharply focused transmit beam is not optimal. Such a sharply focused beam provides a high intensity (near the FDA limits) at the focus, but an intensity that is undesirably low at many other points along the associated receive scan line.

The receive beamformer 16 (FIG. 1) preferably receives samples along an entire scan line for each transmit event. For this reason, it is preferable that the region of insonification within the desired power level range be extended over a substantial portion of the length of the receive scan line. Thus, it is preferable that the intensity of the transmitted ultrasonic energy be substantially uniform and at a high level throughout the field of interest (which is typically a large fraction of the displayed depth).

The delay memory 42 (FIG. 2) preferably stores delay and/or phasing values to provide a controlled spread to the beam intensity in a way to optimize imaging of the contrast agent. Also, by making the intensity of harmonic energy received at the receive beamformer 16 (FIG. 1) more uniform throughout the field of interest, the levels of harmonic backscatter may be better controlled, resulting in manageable voltage swings at the receiver input.

Figure 5:
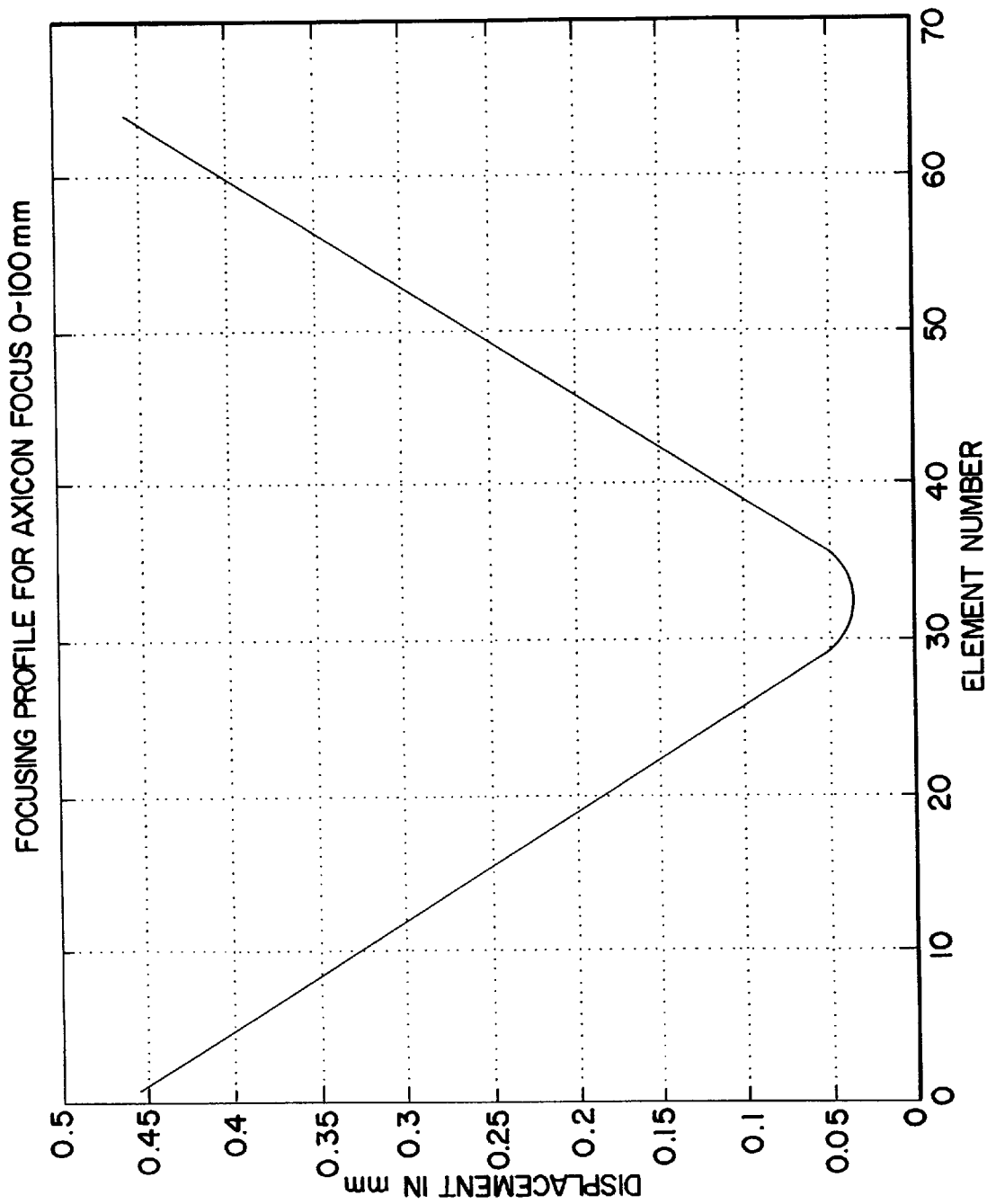
FIG. 5 is a graph of a focusing profile suitable for an axicon focus.

In this embodiment, the delay values stored in the delay memory 42 (FIG. 2) are selectively chosen to spread the beam along the current ultrasound line. One way to accomplish this is to use the well-known axicon focusing arrangement, as described, for example by C. Burckhardt in "Ultrasound Axicon: A Device for Focusing over a Large Depth" (J. Acoust. Soc. of Am., 54, 6, pp. 1628–1630 (1973)). The axicon focusing arrangement may utilize a focusing profile as shown in FIG. 5. Typically, this focusing profile provides a near focal limit corresponding to a circular arc centered on the near local limit. Typically, the delay profile extends linearly outwardly from this circular arc to some outer limit, as shown in FIG. 5.

The objective is to spread the ultrasound energy throughout a region of the target, and many different delay profiles may accomplish this result. For example, the delay profile may be slightly curved, with a nonlinear variation of focal point with respect to transducer element position. There may be an outer focal limit, in which case the delay profile can include a circular portion at the ends of the array.

In many applications, it will be desirable to select the delay values in the delay memory 42 (FIG. 2) such that at least first frequency components of the transmit beam from at least a first plurality of transducers are focused at a first, shorter range, and that at least second frequency components of the transmit beam from at least a second plurality of transducers are focused at a second, longer range. One example is shown in FIG. 6, where substantially all of the ultrasonic energy from the transducers 14a at the end portions of the transducer array 14 are focused at a single longer range X1, and substantially all of the ultrasonic energy from the transducers 14b at central portions of the array are focused at a single, shorter range X2. The power level associated with the frequency component focused at the longer range, X1, may be higher than the power level associated with the frequency component focused at the shorter range, X2. By properly selecting the delay values, a line focus or a multiple-point compound focus may be obtained. When a line focus is used, the line may be straight or curved.

Another approach begins with focal delays required for a chosen focal point in the conventional manner. A random delay error is superimposed on these focal delays to smear or defocus the resulting beam. The greater the degree of defocusing, the more spread out the beam is. Preferably, a user control is provided to allow the user to vary the degree of defocusing by increasing the relative level of the defocusing delays. Also, it is preferable to increase the transmitted energy level to partially compensate for the loss of peak field intensity due to defocusing, either in an automatic (internally programmed) manner or under user control. The defocusing hardware can consist of a modified version of aberration correction hardware in which the delay corrections are pre-programmed random numbers rather than values which are continuously updated, for example by means of cross-correlating the waveforms from adjacent elements.

Conventional imaging at the fundamental frequency using an axicon or defocused beam is known to produce side lobes. However, such side lobes are not anticipated to create substantial problems in this application. Full dynamic receive focusing is preferably performed in the receive beamformer 16 (FIG. 2) to reduce the effect of side lobes in the transmit beam further.

Regardless of the precise configuration of the waveform 80, the waveform 80 preferably provides more uniform field intensity through a usefully extended depth of field. This results in more uniform generation of harmonic energy and possibly a higher overall signal to noise ratio.

An axicon focusing scheme may be used in the elevation direction, if it is desired to increase the dimension of the insonified region in that direction. For similar elevation focusing, a transducer design similar to that in U.S. application Ser. No. 08/675,412 (Atty. Ref. No. 5050/51), assigned to the assignee of the present invention, is used. High frequencies are focused shallowly and low frequencies are focused deeply. Alternatively, a 1.5 D array transducer comprising a small number of elements in the elevation direction is used to form a narrow, well focused elevation beam profile.

The transmit beamformer 40 of FIG. 2 is quite similar to the beamformer shown in FIG. 13 of U.S. Pat. No. 5,608,690, and the techniques described above relating to Gaussian waveforms modified to provide a line focus can be performed in the manner described in the above-identified patent. The optimized transmit beamformers may also be used for harmonic imaging of tissue. With this approach, a plurality of transmit waveforms are provided, each for a respective one of the transducers of the transducer array. This plurality of transmit waveforms includes a central transmit waveform associated with a central one of the transducers. As explained in the above-identified '690 patent, the central transmit waveform preferably comprises a lower frequency component and a higher frequency component, and a lower frequency component of the central transmit waveform occurs earlier in time than the higher frequency component of the central transmit waveform, as shown in FIG. 7. FIG. 7 corresponds to FIG. 11 of above-identified U.S. Pat. No. 5,608,690, and that patent can be referenced for additional information regarding these figures. When the system of U.S. Pat. No. 5,608,690 is adapted for use with this invention, it is preferred that the frequencies along the line focus all be near the fundamental frequency to insanity effectively for harmonic imaging. Other waveform shaping, focusing, and apodization schemes may be used, such as disclosed in U.S. patent application Ser. No. 08/911,973 for an Ultrasonic Harmonic Imaging System And Method Using Waveform Pre-distortion.

Acoustic Transmission and Reception

Referring to FIG. 1, the excitation signals from the transmit beamformer 12 are provided to the transducer 14. For imaging pulsatile targets within the subject (e.g. heart or carotid), gating is preferably used to trigger application of the excitation signals to the transducer 14. In order to further improve three-dimensional imaging, only images corresponding to selected portions of the ECG cycle, the breathing cycle or both are utilized. Both ECG gating and breathing gating are well known in three-dimensional reconstruction of images. See, for example, McCann et al. "Multidimensional Ultrasonic Imaging for Cardiology" at p. 1065. With ECG gating, a window is selected a fixed time duration after the ECG pulse maximum. With breathing gating, it is often simplest to ask the patient to hold his or her breath for the short duration of the ultrasonic scan. Alternatively, chest motion can be recorded using a displacement sensor, and data can be selected for a portion of the breathing cycle. As yet another alternative, the temperature of air in the patient's nostrils is detected.

Based on the gating or other inputs, the excitation signals are provided to the transducer 14. The transducer 14 is of any construction known in the art, such as the one-dimensional, multiple element (array) Acuson 3V2c transducer discussed above. One or more of the elements in the transducer 14 are excited by an excitation signal to produce ultrasonic acoustic waveforms. In particular, the transducer 14 converts these excitation signals into ultrasonic energy that is directed along transmit beams into the subject, such as the body of a medical patient. Scattering sites within the subject, such as contrast agents or tissue in the subject, cause echo information to be returned to the transducer 14. This echo information is converted by the transducer 14 into electrical signals that are applied to the receive beamformer 14.

The receive beamformer 16 is of a construction known in the art, such as an analog or digital receive beamformer capable of processing signals associated with different frequencies. The receive beamformer 16 and the transmit beamformer 12 may comprise a single device. As known in the art, each electrical signal is delayed, apodized, and summed with other electrical signals. An ongoing stream of summed signals represents the ultrasound beam or line, or portions of the lines when multiple transmit focus depths per line are used, received from the body. The receive beamformer 16 passes the signals to the filter block 18.

The filter block 18 passes information associated with a desired frequency band, such as the fundamental band using fundamental band filter 24 or a harmonic frequency band using the harmonic band filter 26. The filter block 18 may be included as part of the receive beamformer 16. Furthermore, the fundamental band filter 24 and the harmonic band filter 26 preferably comprise one filter that is programmable to pass different frequency bands, such as the fundamental, second or third harmonic bands. For example, the filter block 18 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated to baseband by shifting by either the fundamental 2 MHz or the second harmonic 4 MHz center frequencies (the demodulation frequency). Other center frequencies may be used. Signals associated with frequencies other than near baseband are removed by low pass filtering. As an alternative or in addition to demodulation, the filter block 18 provides band pass filtering. The signals are demodulated to an intermediate frequency (IF)( e.g. 2 MHz) or not demodulated and a band pass filter is used. Thus, signals associated with frequencies other than a range of frequencies centered around the desired frequency or an intermediate frequency (IF) are filtered from the summed signals. The demodulated or filtered signal is passed to the signal processor 20 as the complex I and Q signal, but other types of signals, such as real value signals, may be passed.

The signal processor 20 comprises one or more processors for generating two-dimensional Doppler or B-mode information. For example, a B-mode image, a color Doppler velocity image (CDV), a color Doppler energy image (CDE), a Doppler Tissue image (DTI), a Color Doppler Variance image, or combinations thereof may be selected by a user. The signal processor 20 detects the appropriate information for the selected image. Preferably, the signal processor 20 comprises a Doppler processor 28 and a B-mode processor 30. Each of these processors is preferably a digital signal processor and operates as known in the art to detect information. As known in the art, the Doppler processor 28 estimates velocity, variance of velocity and energy from the I and Q signals. As known in the art, the B-mode processor 30 generates information representing the intensity of the echo signal associated with the I and Q signals.

The information generated by the signal processor 20 is provided to the scan converter 22. Alternatively, the scan converter 22 includes detection steps as known in the art and described in U.S. application Ser. No. 08/806,922 (Atty. Ref. No. 5050/189) now U.S. Pat. No. 5,793,701, assigned to the assignee of the present invention. The scan converter 22 is of a construction known in the art for arranging the output of the signal processor 20 into two-dimensional representations or frames of image data. Preferably, the scan converter 22 outputs formatted video image data frames, such as DICOM Medical industry image standard format or a TIFF format. Thus, the plurality of two-dimensional representations are generated. Each of the representations corresponds to a receive center frequency, such as a second harmonic center frequency, a type of imaging, such as B-mode, and positional information. The harmonic based representations may have better resolution and less clutter than fundamental images. By suppressing the harmonic content of the excitation signal, the benefits of harmonic imaging of tissue may be increased.

Alternate Ultrasound System

The transmit beamformer 12 and receive beamformer 16 can take many forms, as described above. Another alternative embodiment is the transmit beamformer described in Cole et al., U.S. patent application Ser. No. 08/286,652, filed Aug. 5, 1994 and now abandoned, and in U.S. patent application Ser. No. 08/432,056, filed May 2, 1995 and now abandoned, both assigned to the assignee of the present invention. This transmit beamformer can be adapted for use with this invention. Once the desired output is defined as described above in terms of very low harmonic signal or any other output, then the ideal output signal is defined in the frequency domain and converted to the time domain. This time domain signal is divided by the carrier to obtain the desired envelope using complex shapes for both the time domain signal and the carrier. This combination of envelope and carrier is programmed into the transmit waveformer, using the various parameters disclosed in the above referenced applications.

The envelope is sampled at a relatively low frequency, and as a result of imperfections in real implementations, remnants of harmonics relating to the sampling frequency of the carrier and the base band signal may appear in the final result. An additional low pass filter may be used to suppress these remnants.

In this example, harmonic energy at the second harmonic is imaged using the receive beamformer described in Wright, et al. U.S. patent application Ser. No. 08/286,658, filed Aug. 5, 1994 and now abandoned, and in U.S. patent application Ser. No. 08/432,615, filed May 2, 1995 and now U.S. Pat. No. 5,685,308, both assigned to the assignee of the present invention. This receive beamformer can be programmed using the parameters disclosed in those applications.

For example, the transmit and receive beamformers discussed above can be operated to transmit at a 1.75 MHz fundamental center frequency and receive at a 3.5 MHz harmonic center frequency using the Acuson 3V2c transducer. For this example, the parameters for these beamformers to generate a B-mode image are shown in Appendix A.

Three-Dimensional Reconstruction

As discussed above, many approaches can be taken in aligning the image data frames to provide the desired three-dimensional reconstruction. Many of the approaches discussed above provide position information associated with the orientation of one image data frame to other image data frames. The position information, such as from a rotatable transducer, is provided from the transducer 14 on a line 32. Alternatively, the position information is calculated off-line or in a processor as discussed in the MULTIPLE ULTRASOUND IMAGE REGISTRATION SYSTEM, METHOD AND TRANSDUCER applications (U.S. application Ser. Nos. 08/621,561 (filed Mar. 25, 1996 abandoned), 08/807,498 (filed Feb. 27, 1997 abandoned) and unassigned (filed herewith: Atty. Ref. No. 5050/204). The position information comprises three components of position (X, Y, Z) and three components of rotation (about X, Y, and Z). Other definitions of position and orientation may be used, such as 2 known points and one origin point on each plane. Furthermore, the position information may be assumed, such as disclosed in Schwartz U.S. Pat. No. 5,474,073.

The position information and the image data frames are provided to a three-dimensional reconstruction computer 34 via a cable or other data link. Preferably, the 3D reconstruction computer 34 is a remote computer for real time or delayed reconstruction. Alternatively, an on-board computer is used. Preferably, the computer 34 is at least an Intel Pentium PC (200+ MHz) or SGI ($O_2$ or Octane for example) with a memory 36. Preferably, the memory 36 is large, such as 128 MB RAM. Image data frames from the scan converter 22 can be compressed using any suitable compression technique such as JPEG prior to transfer. After the image data has been received, it is decompressed. For example, 3D reconstruction can be performed on a remote workstation such as the AEGIS workstation of Acuson Corporation, the assignee of the present invention. Thus, the reconstruction and display of a three dimensional representation is either during the imaging session or after the imaging session.

For reconstruction, the computer 34, with the memory 36, uses the image data frames and the position information to generate information for the three dimensional representation of a volume. Information from the two-dimensional image data frames is converted to a 3D grid, such as a preferred regularly (equal) spaced volume grid. Equal spacing allows for efficient calculations and use with low cost visualization software. One example is shown schematically in FIGS. 8–10. In this example, the image data frames prior to reconstruction are shown schematically in FIG. 8. The image data frame for a central plane is inserted at a plane aligned with the center of the volume, as shown in FIG. 9. Working outwardly from this center plane, successive image data frames are inserted into their appropriate XYZ locations, as a function of the positional information. As shown in FIG. 10, the image data frames are associated with axial rotation about an axis lying in an azimuthal direction along the lens surface of the transducer 14 (FIG. 1). Once all frames have been inserted, intermediate points are calculated using three-dimensional linear interpolation techniques relying on the eight closest known data points.

The computer 34 uses software to construct the 3D representation based on the input information discussed above. Various commercially available software and fixtures are available for 3D reconstruction. For example, TomTec GmbH (Unterschleissheim, Germany) offers software and mechanical fixtures specifically for 3D ultrasound. The software is capable of 3D reconstruction based on several different scan formats, such as rotations and freehand scanning. Life Imaging System Inc. (London, Ontario, Canada) also provides software and mechanical scanning fixtures for 3D ultrasound. VayTek Inc. (Fairfield, Iowa) produces rendering software for a 3D volumetric regularly spaced, orthogonal grid data. As yet another example, Advanced Visual Systems Inc. (Waltham, Mass.) offers an AVS5 software package for constructing and rendering 3D representations from the plurality of image data frames.

Alternatively, the software for reconstruction of the 3D representation is written specifically for the system 10 described above. A standard language, such as C or C++, is used with WindowsNT® (Microsoft) and a graphics Applications Programming Interface (e.g. OpenGL® (Silicon Graphics Inc.)). Other languages, programs, and computers may be used.

Figure 11:
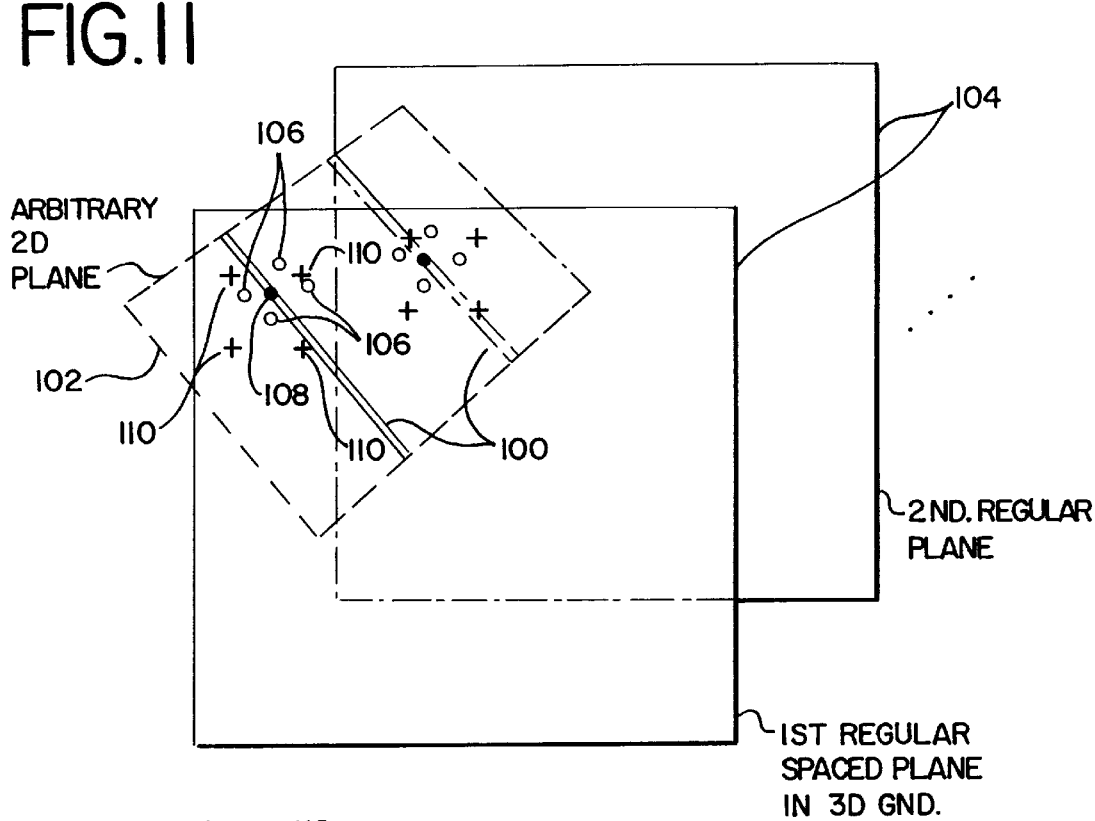
FIGS. 11 and 12 are schematic representations of methods for generating a set of data in a regularly spaced, orthogonal three-dimensional grid.

One approach for generating a 3D data set from arbitrarily spaced image plane data is graphically demonstrated in FIG. 11. Lines 100 corresponding to the intersection between a series of arbitrary planes 102, spaced according to the positional information, and regularly spaced planes 104 of the regularly spaced 3D grid are used. The arbitrary planes 102 may or may not coincide with planes of the 3D grid. Data samples 106 in the arbitrary plane 102 are linearly interpolated with neighboring data samples 106, such as 4 samples, to derive interpolated data samples 108 along the lines 100. A series of interpolated data samples 108 associated with all the regularly spaced planes 104 and the arbitrary planes 102 is obtained. The interpolated data samples 108 are linearly interpolated to generate 3D data samples 110 on the 3D grid. Other methods of interpolation, such as spline fitting, may be used.

Instead of arbitrary planes 104, spaced line data, such as associated with an ultrasound scan line, is preferably used to interpolate to the 3D grid. Thus, the data samples 106 correspond to I and Q data along two or more adjacent scan lines. These data samples are not yet interpolated to the arbitrary two-dimensional planes 102 by scan conversion. Typically, these acoustic data samples 106 are not yet down sampled as is done in scan conversion (such as 12 or more bits of data versus reduced to around 8 bits by the scan-conversion process for compatability with standard displays). Preferably, the data samples 106 are subjected to a bipolar logarithmic compression function (i.e. $\log(-x)=-\log(x)$, where x is positive). Preferably, additional I and Q samples are interpolated between the known I and Q samples. To prevent distortion, the phases of adjacent I and Q beam data are aligned. For a discussion of this phase alignment, see Method and Apparatus for Coherent Image Formation, Wright et al., U.S. Pat. No. 5,623,928, assigned to the assignee of the present invention.

Figure 12:
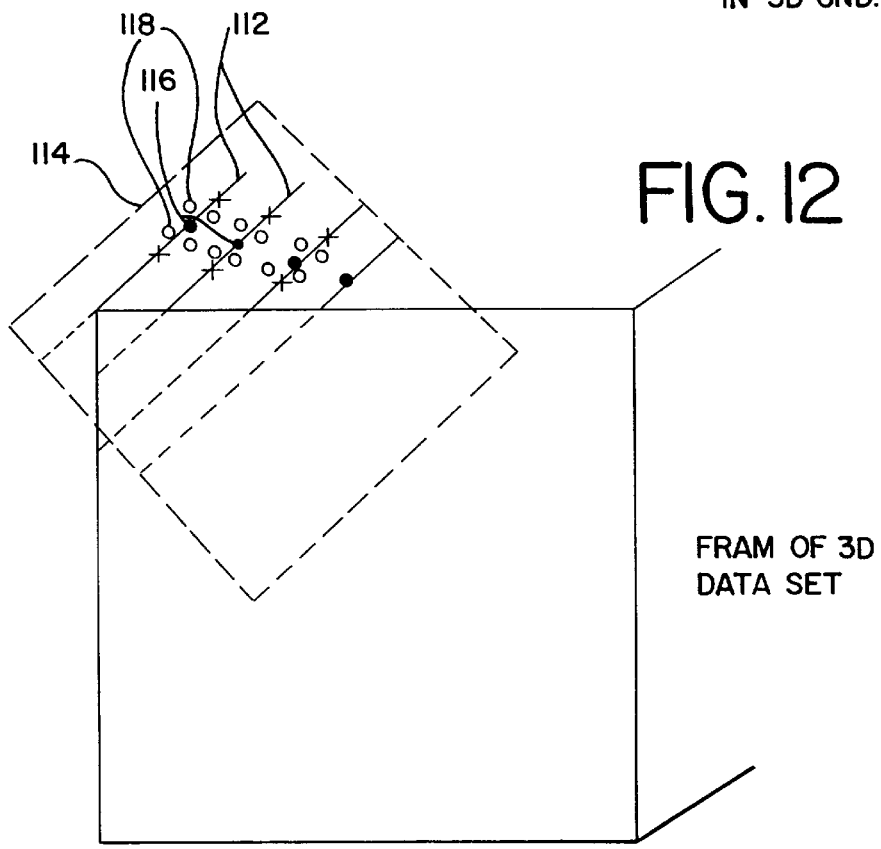

Yet another approach is graphically demonstrated in FIG. 12. A series of parallel lines 112, corresponding to lines within the regularly spaced 3D grid, intersect a series of arbitrary planes 114. At the points of intersection between the lines 112 and the arbitrary planes 114, data samples 116 are interpolated from neighboring image plane data samples 118. Along each line 112, 3D grid data samples are interpolated from the data samples 116. Other approaches to 3D reconstruction may be used, such as a nearest neighbor search (higher speed but inferior spatial accuracy).

The 3D grid of 3D data samples (110 in FIG. 11 and 118 in FIG. 12) obtained by any of the above referenced or other methods may be smoothed or filtered. For example, a 3D low pass filter, such as a 3×3×3 FIR filter), or a median filter, such as 3×3×3 or 5×5×5 filters, are used. Alternatively, the line data or image plane data is filtered prior to 3D reconstruction. The three-dimensional reconstruction may include other structures generated by other methods than 3D grid data interpolated from information signals, such as data associated with a viewing plane selected as the maximum signal along a projection through arbitrary planes as discussed below.

Visualization And Quantification

The 3D grid of 3D data samples (110 in FIG. 11 and 118 in FIG. 12) are used for representing a three-dimensional image or for various quantifications. By reconstructing 3D representations and quantifying using information from harmonic frequencies, such as a 3D harmonic based B-mode image, the image contains less noise or clutter effects and shows more detail of a desired object than a fundamental based image. Clutter in a two-dimensional image partially obscures the image, but since only a cross-section is being examined, the object is still discernible. For 3D reconstruction, the clutter may surround the object so that the object cannot be discerned from the clutter. Thus, harmonic based 3D visualization and quantification may result in more useful 3D representations.

Various visualization software, such as Fortner Research LLC's T3D, and techniques may be used to present the 3D image or reconstruction on a two-dimensional display. Referring to FIG. 1, the computer 34, when operating in a display mode, can select appropriate information from the three-dimensional grid data samples to provide a desired image on a display 38. For example, cross sections can be taken in various planes, including a wide variety of planes selected by the user that do not correspond to the planes of the image data. The selected planes are interpolated from the 3D grid data samples. For 3D imaging, the 3D representation on the display 38 may be rotated, zoomed and viewed in perspective as is well known in the art (e.g. Computer Graphics by Foley, van Dam, Feiner and Hughes, Addison Wesley, 1996, chapter 6). Various techniques for 3D imaging are possible, such as surface renderings and volume rendering displays.

For an example of surface rendering, see "MARCHING CUBES: A HIGH RESOLUTION 3D SURFACE CONSTRUCTION ALGORITHM" by W. E. Lorensen and H. E. Cline, Computer Graphics, Vol. 21, No. 4, July 1987. Once the surfaces are determined, a polygon mesh is formed to represent the surface. The surface is rendered with lighting cues, such as Gouraud or Phong shading. Gouraud shading is generally simpler than Phong shading and may be accelerated with suitable hardware, but Phong shading produces a higher quality image.

As an alternative to the surface rendering discussed above, the polygon mesh is derived by applying border detection to each image plane (two-dimensional representation). For example and referring to FIG. 13, a border 124, such as a vessel border, is determined in each appropriate image plane 122 automatically or by user designation with a mouse or other device. For example, the border 124 corresponds to the edges of tissue structure, edges of a chamber or blood filled region (such as with contrast agents), or an edge of an area not filled with blood or a contrast agent (such as unhealthy tissue in the heart muscle). The border 124 may be an enclosed border as shown or may end at another location, such as a user selected location. A data sample 120, such as a first data sample, is associated with a topmost or a beginning detected sample in each image plane 122. In a particular direction, such as clockwise or counterclockwise, the border 124 is divided into a fixed number of points 126 and associated equally spaced segments, such as 50 points. Each segment is in number sequence. The polygon mesh is formed by logically linking the numbered points 126 from image plane to image plane (e.g. Frame #1, point #1 is linked to Frame #2, point #1). The links and the segments define the polygon mesh. Diagonal links may be inserted into the rectangular mesh elements to produce a conventional triangular mesh.

Another technique for representing the 3D data samples on the display 38 is volume rendering, such as alpha bending, maximum intensity or minimum intensity projection. Based on a range of viewing angles, such as 120 degrees, and the incremental values between each viewing angle, such as 1 degree, a number of three dimensional projections is determined, such as 121. Each projection corresponds to a viewing plane that is perpendicular to the viewing angle. The 3D data samples at each viewing angle are summed along the lines of vision or "into" the 3D grid or viewing plane. Thus, a value for each region in a viewing plane is determined. For alpha bending, a weighting is applied to each 3D data sample. The weighting values are selected to emphasize near objects. Thus, a sense of front and back regions is created. Alpha bending allows viewing of internal objects relative to surrounding objects. Instead of alpha bending, maximum, minimum or other functions may be used. For maximum or minimum intensity projection, the maximum or minimum 3D data sample, respectively, is used instead of the summation along each line. Other viewing techniques may be used.

The 3D data samples may include information associated with a plurality of processing modes, such as (1) harmonic B-mode information and (2) harmonic or fundamental Doppler information or fundamental B-mode information. For example, the 3D data samples include a harmonic B-mode value and a separate color Doppler velocity value.

A chamber or other object may be visualized as described above, such as a surface rendering, as a function of time. For example, the 3D representation is displayed as a series of images within a heart cycle. This dynamic 3D representation indicates changes in shape and volume over time.

The 3D grid data or the volume rendering data is also or independently used to calculate various quantities, such as a volume. For example, based on border detection, such as discussed above for surface rendering, or selection of region of interest by the user, the volume of a chamber (surface bounded or region of interest bounded volume) is calculated. The number of volumetric elements, such as voxels, within the surface or region are summed. The sum is multiplied by a volume associated with each volumetric element. Other quantities may be calculated. For example, the volume is calculated as a function of time. This time based information is displayed as a series of quantities or as a waveform (graph of volume as a function of time). As another example, a ratio of the volume change over a heart cycle to the maximum volume over the same heart cycle is determined. The ratio of heart chamber volume change (left ventricle) to maximum chamber volume provides an ejection fraction and is a quantity used in the assessment of heart health. The ratio may then be determined as a function of time or a mean value over a plurality of heart cycles. Any of the quantities may be determined during or after an imaging session.

Other quantities determined from the 3D grid data or surface rendering data is the thickness and volume of the heart muscle. A surface mesh or rendering is produced of the outer and inner surfaces of a heart chamber. Using the 3D location of both surfaces relative to each other, the thickness is determined at any of various locations. The volume of the heart muscle, the difference in volume associated with the inner surface and the volume associated with the outer surface, may also be calculated. The change in thickness or difference in volumes as a function of time may also be determined. A discussion of heart wall measurements is found in Sheehan, U.S. Pat. No. 5,435,310.

Various quantities corresponding to three-dimensional space, such as volume, may also be quantified without constructing the 3D representation or 3D grid data discussed above. Thus, the image plane data output from the scan converter 22 (FIG. 1) or line data output from the signal processor 20 (FIG. 1) is used to calculate the quantity, such as volume. The border or surface is automatically determined based on signal level or manually determined. For example, automatic border detection determines the border or surface based on a threshold value (e.g. median or mean value). One such automatic border detection used in the presence of ultrasound speckle as applied to the 2D planes is disclosed by H. E. Melton, Jr. and D. J. Skorton in "REAL-TIME AUTOMATIC BOUNDARY DETECTION IN ECHOCARDIOGRAPHY", 1992 Ultrasonics Symposium, p 1113–17.

As another example, the polygon mesh surface rendering technique using border detection on image plane data discussed above is used to define the 3D border without reconstruction of the 3D representation or grid data. Assuming the image planes are generally parallel, the volume of each plane is determined. The sum of the pixel areas or data within the border for each image plane is multiplied by a plane thickness to obtain plane volume. The results of each multiplication are integrated over all the image planes (Simpson's Integration) to find the total volume of the region.

Referring to FIG. 14, if the image planes were acquired using a rotatable transducer (planes not parallel), then the volume is split into prism shaped volumetric elements 140. The axis of rotation 142 is treated as a vertical line of the element 140. A length, L, is calculated as the geometric mean length between the axis 142 and four ranges 144 associated with the border in two adjacent image planes 146. $L = \sqrt[4]{ABCD}$, where A and C are in one image plane and B and D are in another. The angle, θ, between the image planes is based on the known positional information. The height, H, of each element 140 is the known distance between two adjacent scan lines within an image plane. The volume of each prism is ½ $L^2 H \sin\theta$. The total volume within the 3D border or surface is the sum of the component prism volumes. This calculation assumes the border is intersected by the axis of rotation. If the axis of rotation is outside the border detected region, the volume of the prism extending from the axis to a "nearer" surface 150 is subtracted from the volume of the prism extending from the axis to "further" surface 152.

Composite 3D Representation

Penetration into tissue is less for harmonic imaging as compared to fundamental imaging. The higher frequency harmonic signals are more severely attenuated as a function of distance. Further, only a fraction of the available input fundamental energy is converted to harmonic energy. While the advantages of harmonic imaging typically outweigh the loss of penetration, a composite imaging technique may be used for imaging volumes or space with greater depths. The composite imaging includes imaging in the same mode, such as B-mode, but at different frequencies for a near field region (harmonic frequency band) and a far field region (fundamental frequency band). For a discussion of composite two-dimensional imaging, see U.S. application Ser. No. 08/904,825 (Atty. Ref. No. 5050/227) for ULTRASONIC IMAGING METHOD AND SYSTEM, filed Aug. 1, 1997, assigned to the assignee of the present invention, the disclosure of which is herein incorporated by reference.

To generate the composite image, the filter block 18 comprises a time varying filter. As shown in FIG. 1, the output of the receive beamformer 16 applied to the filter block 18 includes ultrasonic echo information at both the fundamental and the harmonic frequency bands. As shown in FIG. 1, the filter block 18 is controlled such that the passband of the filter block 18 changes with time. The passband of the filter block 18 is centered at the harmonic frequency, 2 $f_0$, at shorter ranges along a given receive beam, and at the fundamental frequency, $f_0$, for larger ranges of the same receive beam. Alternatively, echo information associated with short ranges is switched to the harmonic filter 26, and echo information associated with long ranges is switched to the fundamental filter 24. Thus, the output of the filter block 18 is fundamental components of the received echo information at longer ranges and harmonic components of the received echo information for shorter ranges. The harmonic and fundamental components may be normalized and summed to result in frequency compounding and associated speckle reduction. This compounding is used over the region for which both the fundamental and harmonic components exceed noise levels.

This composite 3D representation is characterized by a near-field region, a far-field region, and an intermediate region situated between the near and far-field regions. The terms near-field and far-field are not intended to define any specific ranges. Rather, the key characteristic is that the near-field region is associated with shorter ranges than the far-field region. The near-field region is spatially distinct from the far-field region, and both regions are formed using a common imaging mode. For example, all three of the regions may be formed as B-mode image regions or color Doppler image regions.

Because the time varying filter block 18 selectively passes echo information centered at the harmonic frequency 2 $f_0$ for shorter ranges while blocking returning echo information centered at the fundamental frequency $f_0$, the near-field region emphasizes and is primarily modulated in response to received ultrasonic echo information in the harmonic frequency band. Similarly, since the time varying filter block 18 passes echo information centered at the fundamental frequency $f_0$ and blocks echo information centered at the harmonic frequency 2 $f_0$ for longer ranges of each receive beam, the far-field region emphasizes and is primarily modulated in response to echo information in the fundamental frequency band. In this way, the imaging benefits of harmonic imaging are obtained for the near-field, where they are most useful, while the penetration advantages of fundamental imaging are obtained for the far-field.

The depth and associated time at which the transition from harmonic to fundamental imaging is made is best determined from experimentation, and will vary based on the frequencies and the transducers being used. The signal to noise ratio of the harmonic band may be used to determine the depth for switching or changing the filtering of the filter block 18. As the system makes a transition from harmonic imaging in the near-field to fundamental imaging in the far-field, a significant change (increase) in apparent signal level will appear due to the reduced attenuation of the fundamental component. In order to avoid a bright region appearing in the image at the far-field, it is preferred to apply depth dependent gain to the signals to make the image more uniform. In some respect, this use of depth dependent gains is similar to focal gain compensation, and manually controlled depth gain controls are well known to those skilled in the art.

In the intermediate region, a mixture of the fundamental and harmonic components will be displayed. The proportion of the contribution of each of these components, as functions of depth, can best be determined from experimental observation.

While the invention has been described above by reference to various embodiments, it will be understood that many changes and modifications can be made without departing from the scope of the invention. For example, the 3D reconstruction may be based on a transducer or array transducer mechanically scanned in two dimensions or an electronically scanned 2D array transducer.

It is therefore intended that the foregoing detailed description be understood as an illustration of the presently preferred embodiments of the invention, and not as a definition of the invention. It is only the following claims, including all equivalents, that are intended to define the scope of this invention.

I claim:

1. A method for calculating a volume quantity with a medical ultrasound system, the method comprising the steps of:

(a) transmitting ultrasonic energy at a first frequency band into a subject during said imaging session, said subject being free of added ultrasound contrast agent throughout the entire imaging session;

(b) receiving ultrasonic echo information associated with said transmitted ultrasonic energy;

(c) isolating from said echo information a plurality of information signals associated a second frequency band and a three-dimensional region of the subject, said second frequency band comprising a harmonic band of said fundamental frequency band;

(d) calculating a volume quantity as a function of said information signals; and (e) displaying the volume quantity.

2. The method of claim 1 wherein the step (d) comprises the steps of (f) determining a region of interest of said image and (g) summing volumes of each volumetric element within said region of interest.

3. The method of claim 2 wherein the step (f) comprises using automatic border detection.

4. The method of claim 1 wherein the step (e) comprises displaying said volume quantity during said imaging session.

5. The method of claim 1 wherein the step (e) comprises displaying said volume quantity after said imaging session.

6. The method of claim 1 wherein the step (d) comprises determining a time sequence of said volume.

7. The method of claim 6 wherein the step (d) comprises determining a ratio related to volume change over a heart cycle to a maximum volume over said heart cycle.

8. The method of claim 7 wherein the step (d) further comprises determining a mean of said ratio as a function of a plurality of heart cycles.

9. The method of claim 1 wherein the step (d) comprises calculating said quantity from said information signals, said information signals comprising line data.

10. The method of claim 1 wherein the step (d) comprises calculating said quantity from said information signals, said information signals comprising three-dimensional grid data.

* * * * *

UNITED STATES PATENT AND TRADEMARK OFFICE
CERTIFICATE OF CORRECTION

PATENT NO. : 5,924,991
DATED : July 20, 1999
INVENTOR(S) : John A. Hossack et al.

It is certified that error appears in the above-identified patent and that said Letters Patent is hereby corrected as shown below:

On the Title Page

Column 2, line 4, under "OTHER PUBLICATIONS", please change "Propogation" to --Propagation--.

Column 2, line 7, under "OTHER PUBLICATIONS", please change "B" to --B.--.

Page 2, column 2, line 32, please change "Specimins" to --Specimens--.

Page 2, column 2, line 37, please change "agenst" to --agents--.

Page 2, column 2, line 61, please change "pp." to --pgs.--.

Page 3, column 1, line 8, please change "sperical" to --spherical--.

Page 3, column 2, line 7, please change "Isreal" to --Israel--.

Page 3, column 2, line 13, please change "pp." to --pgs.--.

Column 3, line 44, please change "1996and" to --1996 and--.

UNITED STATES PATENT AND TRADEMARK OFFICE
CERTIFICATE OF CORRECTION

PATENT NO. : 5,924,991
DATED : July 20, 1999
INVENTOR(S) : John A. Hossack et al.

It is certified that error appears in the above-identified patent and that said Letters Patent is hereby corrected as shown below:

Column 4, line 10, please change "arc" to --are--.

Column 4, line 14, please change "Colo" to --Colorado--.

Column 8, line 14, please change "oil" to --on--.

Column 9, line 42, please change "energy-from" to --energy from--.

Column 10, line 48, please change "insanity" to --insonify--.

Column 13, line 17, please change "(filed Mar." to --filed Mar.--.

Column 14, line 12, please change "Mass." to --MA--.

Signed and Sealed this

Sixteenth Day of January, 2001

Attest:

Q. TODD DICKINSON

*Attesting Officer*  *Commissioner of Patents and Trademarks*